(12) United States Patent
Rubenstein et al.

(10) Patent No.: US 8,008,093 B2
(45) Date of Patent: Aug. 30, 2011

(54) INHIBITION OF HSP27 PHOSPHORYLATION FOR THE TREATMENT OF BLISTERING DISORDERS

(75) Inventors: David Scott Rubenstein, Chapel Hill, NC (US); Paula Berkowitz, Chapel Hill, NC (US); Peiqi Hu, Chapel Hill, NC (US); Luis Alberto Diaz, Chapel Hill, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 961 days.

(21) Appl. No.: 11/791,903

(22) PCT Filed: Dec. 2, 2005

(86) PCT No.: PCT/US2005/043787
§ 371 (c)(1), (2), (4) Date: Oct. 26, 2007

(87) PCT Pub. No.: WO2006/071456
PCT Pub. Date: Jul. 6, 2006

(65) Prior Publication Data
US 2008/0207519 A1 Aug. 28, 2008

Related U.S. Application Data

(60) Provisional application No. 60/632,730, filed on Dec. 2, 2004.

(51) Int. Cl.
*G01N 33/564* (2006.01)
(52) U.S. Cl. .................................... 436/506
(58) Field of Classification Search .................. None
See application file for complete search history.

(56) References Cited

U.S. PATENT DOCUMENTS 5,837,224 A * 11/1998 Voorhees et al. ............... 424/59
2002/0028798 A1 3/2002 Demopulos et al.

OTHER PUBLICATIONS

Hirano, 2002, Journal of surgical research, 102, 77-84.*
Horio, 1987, Photodermatology, 4, 246-251.*
Retrieved from: http://web.archive.org/web/20040807044246/en.wikipedia.org/wiki/Main_Page, 2004, 3 pages [Retrieved on Nov. 10, 2010].*
Notification Concerning Transmittal of International Preliminary Report on Patentability (Chapter I of the Patent Cooperation Treaty) corresponding to a PCT Application No. PCT/US2005/043787 dated Jun. 14, 2007.
Barr et al. Glucocorticoids regulate the synthesis of HSP27 in rat brain slices. *Brain Research*, vol. 847, (1999), pp. 9-17.
Garrod et al. *Gesmosomal cadherins. Current Opinion in Cell Biology*, vol. 14, (2002), pp. 537-545.
Hirano et al. MAP kinase pathways involving Psp27 regulate fibroblast-mediated wound contraction. *Journal of Surgical Research*, vol. 102, (2002), pp. 77-84.
International Search Report corresponding to PCT Application No. PCT/US05/43787 dated Jul. 31, 2006.
Internationally Preliminary Report on Patentability corresponding to PCT Application No. PCT/US05/43787 dated Jun. 5, 2007.
Leal et al. Lead-stimulated p38MAPK-dependent Hsp27 phosphorylation. *Toxicology and Applied Pharmacology*, vol. 178, (2002), pp. 41-55.
Written Opinion of the International Searching Authority corresponding to PCT Application No. PCT/US05/43787 dated Jul. 31, 2006.

* cited by examiner

*Primary Examiner* — Cecilia Tsang
*Assistant Examiner* — Satyanarayana Gudibande
(74) *Attorney, Agent, or Firm* — Jenkins, Wilson, Taylor & Hunt, P.A.

(57) ABSTRACT

A method of treating a blistering disorder, which includes administering to a target tissue in a subject in need thereof an effective amount of a composition that inhibits activation of the HSP27 phosphorylation pathway.

13 Claims, 15 Drawing Sheets

| | PV IgG | PV IgG + Inh |
|---|---|---|
| Ecad |  |  |
| Ker |  |  |
| Ecad +Ker |  |  |

SEQUENCE LISTING

```
<160> NUMBER OF SEQ ID NOS: 2

<210> SEQ ID NO 1
<211> LENGTH: 18
<212> TYPE: PRT
<213> ORGANISM: Artificial Sequence
<220> FEATURE:
<223> OTHER INFORMATION: A synthetic peptide based on the human
      MAPKAPK-2 polypeptide (amino acid residues 344-360) with a
      cysteine added.

<400> SEQUENCE: 1

Cys Glu Asp Lys Glu Arg Trp Glu Asp Val Lys Glu Glu Met Thr Ser
1               5                   10                  15

Ala Leu

<210> SEQ ID NO 2
<211> LENGTH: 13
<212> TYPE: PRT
<213> ORGANISM: Artificial Sequence
<220> FEATURE:
<223> OTHER INFORMATION: Synthetic peptide analogous to the HSP25
      blocking peptide isolated from Ehrlich ascites tumor cells

<400> SEQUENCE: 2

Lys Lys Lys Ala Leu Asn Arg Gln Leu Gly Val Ala Ala
1               5                   10
```

INHIBITION OF HSP27 PHOSPHORYLATION FOR THE TREATMENT OF BLISTERING DISORDERS

CROSS REFERENCE TO RELATED APPLICATIONS

This application is based on and claims priority to U.S. Provisional Application Ser. No. 60/632,730, filed Dec. 2, 2004, herein incorporated by reference in its entirety.

GRANT STATEMENT

This work was supported by grant numbers RO1-AR302, RO1-AR32599, T32 AR07369, Al49427-01, Al40768, and AR30281 from the U.S. National Institutes of Health (NIH). Thus, the U.S. government has certain rights in the presently claimed subject matter.

TECHNICAL FIELD

The presently claimed subject matter generally relates to the treatment of blistering disorders in a subject. More particularly, the methods of the presently disclosed subject matter relate to targeting desmosome signaling via inhibiting the activation of the HSP27 phosphorylation pathway to treat desmosome-associated blistering disorders.

TABLE OF ABBREVIATIONS

| | |
|---|---|
| 1D | 1-dimensional |
| 2D | 2-dimensional |
| $CaCl_2$ | calcium chloride |
| cm | centimeter |
| con-IgG | control IgG |
| DMEM | Dulbecco's Modified Eagle Medium |
| DMSO | dimethylsulfoxide |
| dsg1 | desmoglein 1 |
| dsg3 | desmoglein 3 |
| DTT | dithio-threitol |
| ECL | enhanced chemiluminescence |
| EDTA | ethylenediaminetetra-acetic acid |
| EGF | epidermal growth factor |
| EGFR | epidermal growth factor receptor |
| ELISA | enzyme linked immunosorbent assay |
| g | gram |
| $H_3PO_4$ | phosphoric acid |
| hr | hour |
| HSP27 | heat shock protein 27 |
| HUVEC | human umbilical vein endothelial cell |
| $^{125}I$ | iodine 125 |
| $^{131}I$ | iodine 131 |
| IgG | immunoglobulin G |
| IF | immunofluorescence |
| Inh | inhibitor |
| IPG | immobilized pH gradient |
| kDa | kilodalton |
| L | liter |
| M | molar |
| MALDI | matrix assisted laser desorption/ionization |
| MAPK | mitogen activated protein kinase |
| MAPKAP 2 | mitogen activated protein kinase activated protein kinase 2 |
| mCi | millicurie |
| mg | milligram |
| ml | milliliter |
| mM | millimolar |
| nm | nanometer |
| MS | mass spectrometry |
| $^{32}P$ | phosphorus 32 |
| p38MAPK | p38 MAP kinase |
| PAGE | polyacrylamide gel electrophoresis |
| PBS | phosphate buffered saline |
| PBST | phosphate buffered saline with Triton X-100 |
| PKB | protein kinase B |
| PMSF | phenylmethylsulfonyl fluoride |
| PV | pemphigus vulgaris |
| PVDF | polyvinylidine difluroide |
| s.c. | subcutaneous(ly) |
| S.D. | standard deviation |
| SDS | sodium dodecyl sulfate |
| TOF | time of flight |
| Tm | melting temperature |
| μg | microgram |
| μl | microliter |
| μM | micromolar |

BACKGROUND

A desmosome is a structure that forms a site of adhesion between two adjacent cells, and comprises a dense plate in each adjacent cell separated by a thin layer of extracellular material. The desmosome further comprises a molecular complex of cellular adhesion proteins and linking proteins that append the cell surface adhesion proteins to intracellular keratin cytoskeletal filaments within a cell. Thus, the basic components of the desmosome are the desmosomal plaque and the associated transmembrane adhesion molecules which function to connect neighboring desmosomes. When the desmosomes that connect adjacent epithelial cells do not function properly, epidermal skin layers can pull apart to allow abnormal movements of fluid within the skin, which can result in blisters and other tissue damage.

In a subject afflicted with an autoimmune disorder, the immune system typically does not distinguish between the subject's own antigens and foreign antigens, resulting in recognition of autologous tissues or soluble molecules as if they were foreign. Subsequent immune responses to the autologous cells or tissue can cause autologous tissue destruction or inflammatory reactions normally reserved for foreign organisms, pathogens, cells or tissue. In autoimmune bullous disorders, one or more components of the desmosome can become the target of specific autoantibodies and thus trigger expansion of the disorder. One particular example of an autoimmune bullous disorder is pemphigus vulgaris, a disorder in which antibodies to the transmembrane protein desmoglein 3 (dsg3) play a role in the disruption of desmosomes and ultimately cell-cell detachment, resulting in the formation of intraepidermal clefts, vesicles or bullae (which can be collectively referred to herein as "blisters").

To elaborate, pemphigus vulgaris is an uncommon, potentially fatal, autoimmune skin disorder characterized by the presence of bullae on apparently healthy skin and mucus membranes wherein a patient's own circulating antibodies attack the points of adhesion of epithelial cells and mucous membranes. The primary lesions associated with pemphigus vulgaris often occur first in the mouth, where they soon rupture and remain as chronic, often painful, erosions for variable periods of time before the skin is affected. On the skin, the bullae typically arise to leave a raw, denuded area and crusting upon rupture. In human pemphigus vulgaris disorders, pathogenic antibodies bind the desmosomal cadherin protein desmoglein-3 (dsg3) causing epidermal cell-cell detachment, ultimately resulting in blisters on the associated tissue.

There are limited treatment options for many blistering disorders (including pemphigus vulgaris). Methods of treatment currently employed in the art include heavy doses of corticosteriods and azathioprine, with relapses common after therapy is stopped. Secondary infection is frequent due to the immune suppression associated with these drugs. Further, these drugs have limited efficacy, toxic side effects, and tend to induce a global immunosuppression. Thus, additional and/or more effective treatment options represent a long-felt and ongoing need in the art.

SUMMARY

Disclosed herein are methods of treating a blistering disorder, comprising administering to a target tissue in a subject in need thereof an effective amount of an composition that inhibits activation of an HSP27 phosphorylation pathway in a target tissue.

Also disclosed herein are methods of modulating the HSP27 phosphorylation pathway, comprising contacting a component thereof selected from the group consisting of p38 MAPK, MAPKAP kinase 2, HSP27, and combinations thereof with a modulator to modulate the pathway, wherein the modulator binds with specificity to the component.

Additionally disclosed herein are methods of reducing end organ damage in a subject suffering from an autoimmune disorder, comprising administering to a target tissue of an end organ in the subject an effective amount of a composition that inhibits activation of a HSP27 phosphorylation pathway in the target tissue.

Accordingly, it is an object of the presently disclosed subject matter to provide a novel method of inhibiting HSP27 phosphorylation for the treatment of blistering disorders.

An object of the invention having been stated hereinabove, and which is addressed in whole or in part by the present invention, other objects will become evident as the description proceeds when taken in connection with the accompanying examples and drawings as best described hereinbelow.

BRIEF DESCRIPTION OF THE DRAWINGS

FIG. 1A presents a set of autoradiograms (25 μM IgG) indicating that relative to buffer and normal IgG controls, the pemphigus vulgaris IgG treated keratinocytes show increased phosphorylation in the proteins corresponding to spots 2, 3, and 5. In contrast, no notable difference in spots 1 and 4 were observed between pemphigus vulgaris IgG and control treated cells. Phosphorylation of spots labeled with an asterisk (*) did not change across time, dose, nor culture conditions and serve as internal controls.

FIG. 1B is a series of enlargements of regions of interest from the autoradiograms of FIG. 1A.

FIG. 1C is a series of bar graphs illustrating that pemphigus vulgaris IgG induced protein phosphorylation is dose dependent. Keratinocytes, cultured in $^{32}[P]$-$H_3PO_4$, were exposed to 5, 10, or 25 μM pemphigus vulgaris IgG (shaded bars) or control IgG (clear bars) for 30 mins at 37° C. Extracts were then separated on 2D gels, and radioactivity in each spot was quantified by phosphoimage analysis. Each data point represents the average of 3 independent experiments; standard deviation is shown.

FIG. 3A is a series of autoradiograms of Western blots of 2D gels. The third and most acidic HSP27 charge isoform (P2) is shown to be increased in the PV IgG treated cells. P0, P1, and P2 designations correspond to non-phosphorylated HSP27 and two phosphorylated HSP27 isoforms, respectively, and were assigned by correlating the 2D gel migration patterns of $^{32}[P]$-labeled proteins with HSP27 immunoreactivity.

Figure 1A:
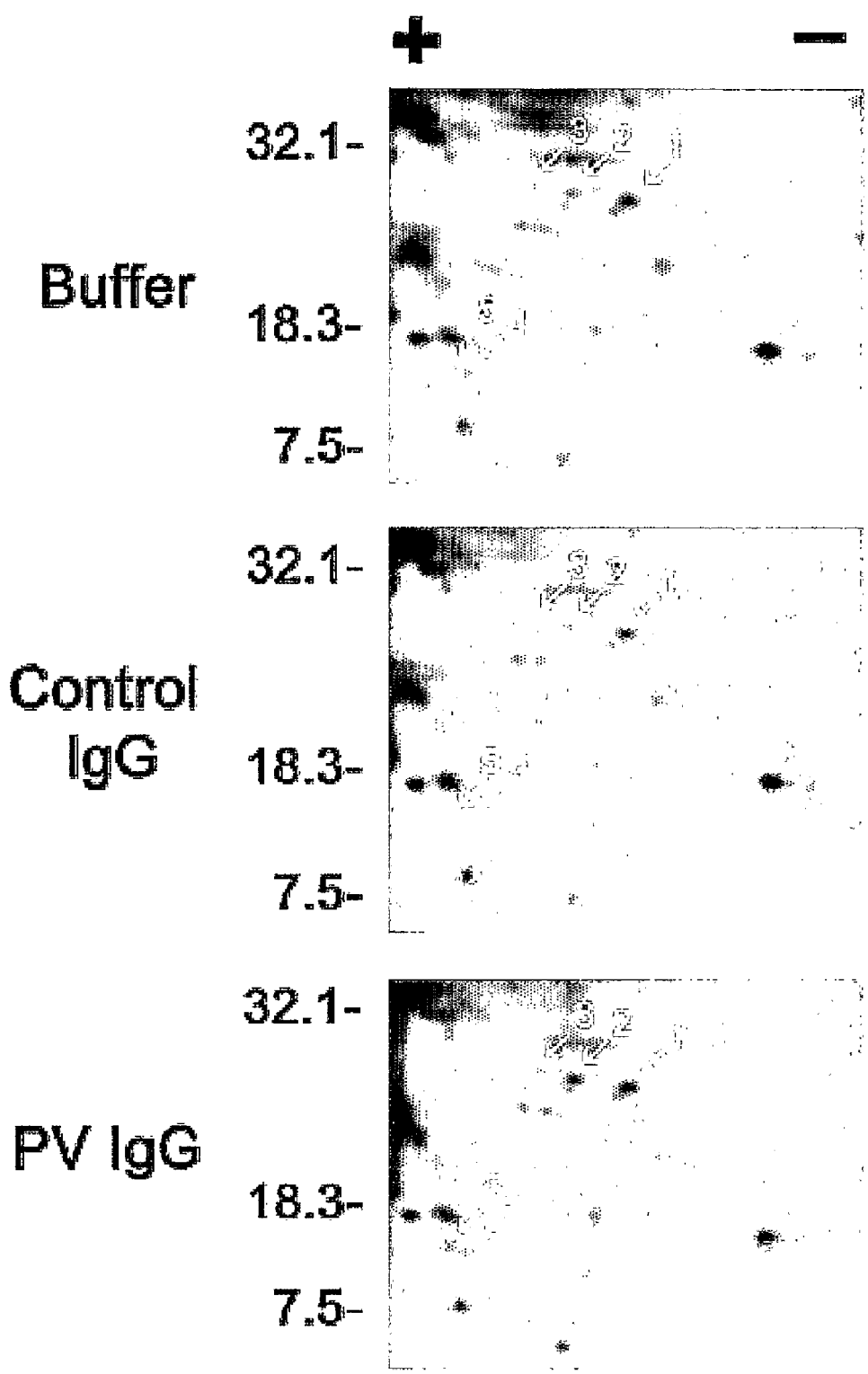
FIGS. 1A-1C present data showing that pemphigus vulgaris IgG alters cellular phosphorylation patterns. Normal human keratinocytes, cultured in the presence of $^{32}[P]$-$H_3PO_4$, were exposed to pemphigus vulgaris IgG, IgG or buffer for 30 mins at 37° C. and extracts separated by 2D gel electrophoresis. The pemphigus vulgaris IgG treated keratinocytes show increased phosphorylation in the proteins corresponding to spots 2, 3, and 5. pemphigus vulgaris IgG induced protein phosphorylation is dose dependent.
Figure 1B:
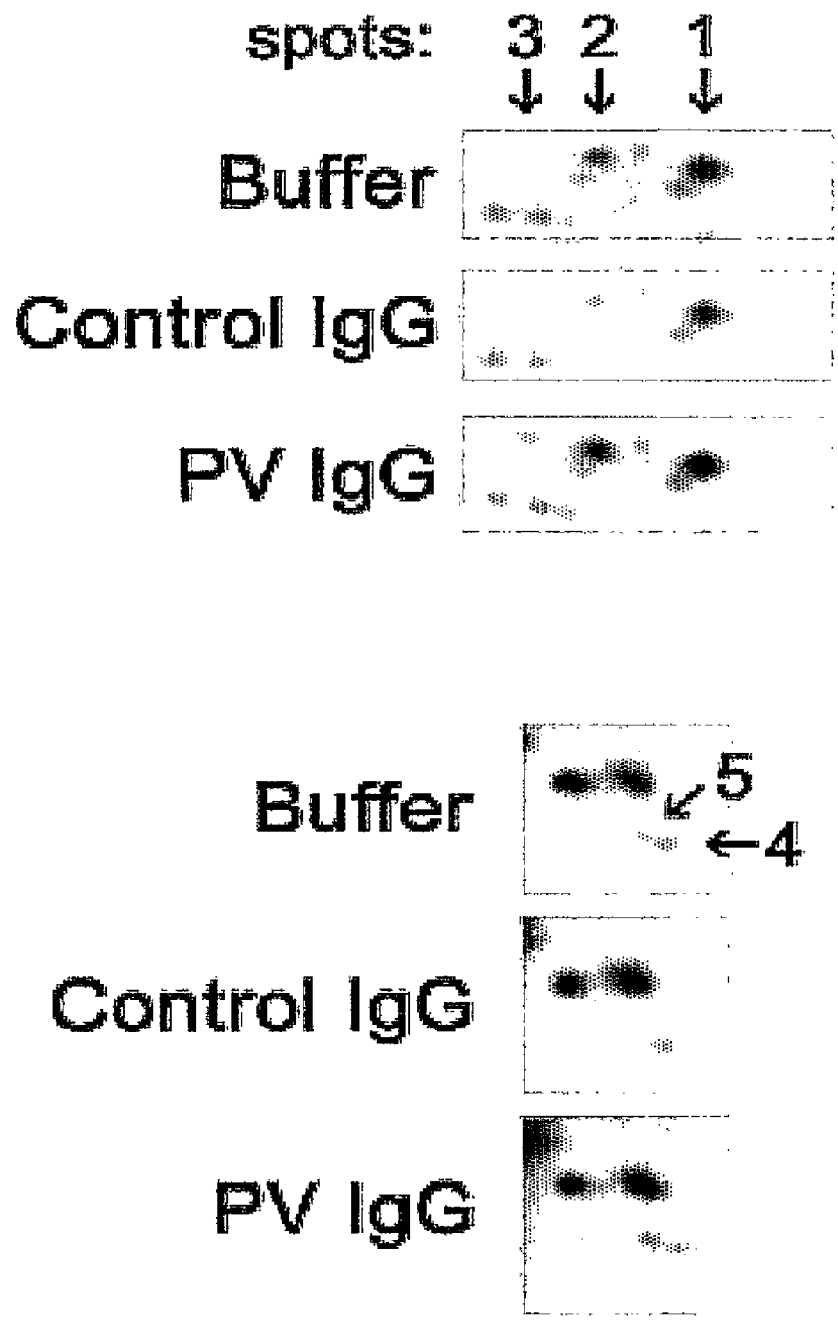
Figure 1C:
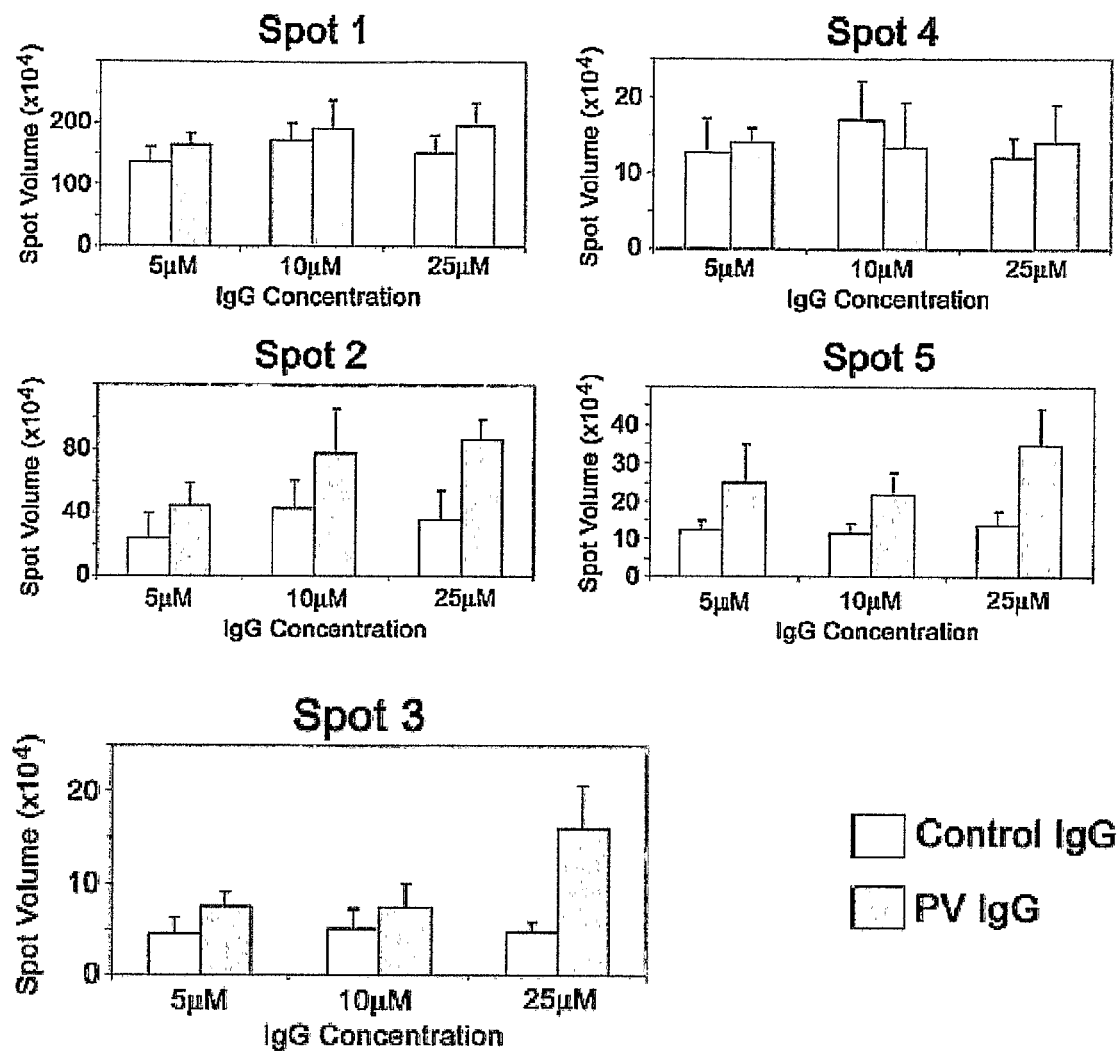

The non-phosphorylated isoform (P0) was not visualized in the autoradiograms. P1 and P2 correspond to spots 1 and 2, respectively, in the autoradiograms of the $^{32}[P]$-labeled extracts (FIGS. 1A-1C).

Figure 3:
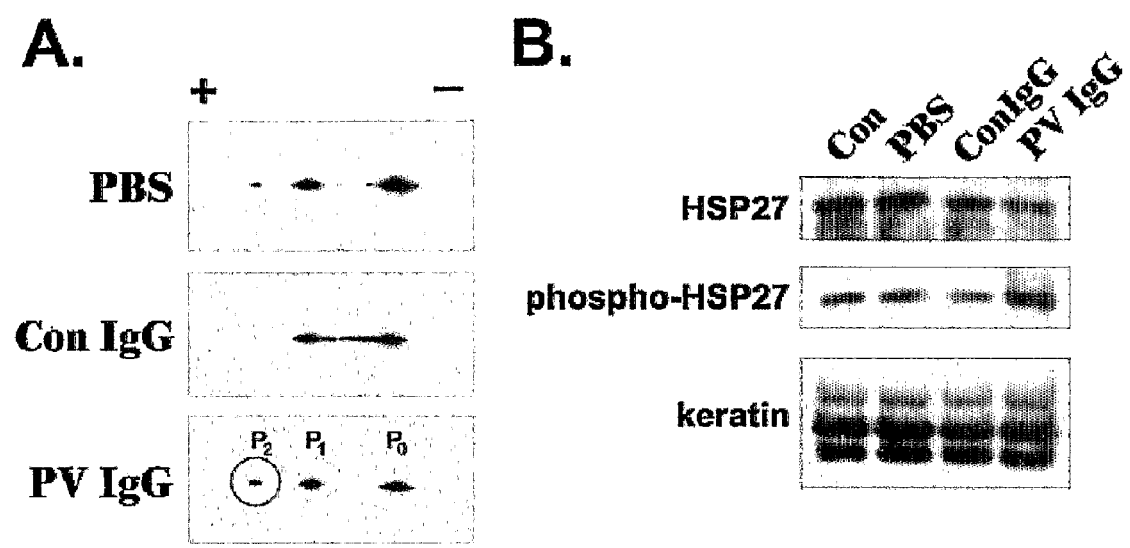
FIGS. 3A and 3B demonstrate that increased phospho-HSP27 immunoreactivity is present in PV IgG treated keratinocytes. Keratinocytes were treated with 25 μM PV IgG, 25/μM control IgG (Con IgG), or buffer controls (PBS) for 30 mins at 37° C.

FIG. 3B is a series of autoradiograms of Western blots of 1D SDS-PAGE gels. Extracts (15 μg protein/lane) from cells incubated with PV IgG show increased phospho-HSP27 immunoreactivity compared to non-treated control (Con), mock treated (PBS), or control IgG (Con IgG) treated cells. Blots were stripped and reprobed with anti-HSP27 (HSP27) and anti-pan keratin (keratin) antibodies to demonstrate equal loading.

Figure 4:
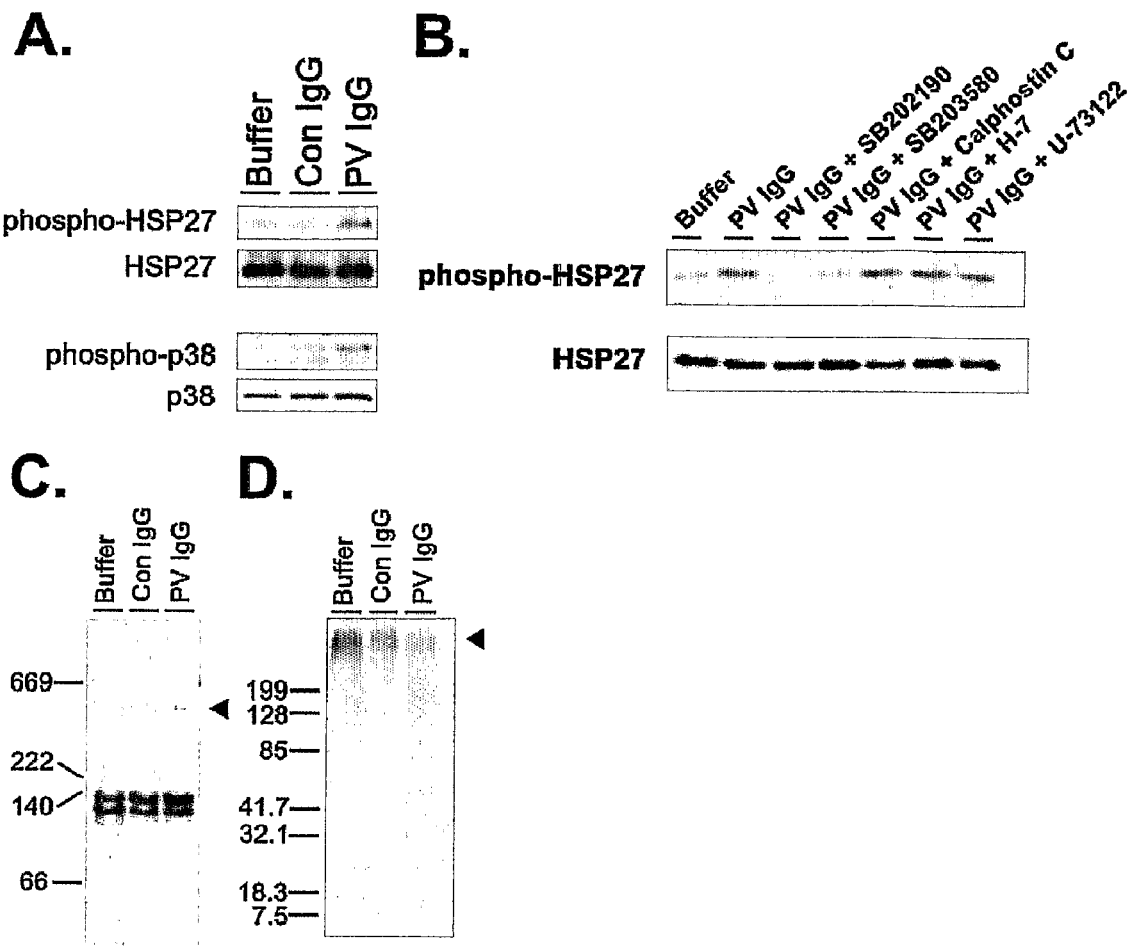

FIG. 4A presents autoradiograms of immunoblots demonstrating that p38MAPK is phosphorylated in PV IgG treated keratinocytes. Cells were exposed to 25 μM PV IgG, control IgG or buffer for 30 mins at 37° C. Extracts (15 μg protein/lane) were separated by 10% SDS-PAGE followed by immunoblotting with antibodies to HSP27, phospho-HSP27, p38MAPK, and phospho-p38MAPK. Increased phospho-HSP27 and phospho-p38MAPK immunoreactivity is detected in the PV IgG treated cells.

FIG. 4B presents autoradiograms of immunoblots demonstrating that inhibitors of p38MAPK block PV IgG induced HSP27 phosphorylation.

Cells were preincubated for 60 minutes at 37° C. with the p38MAPK inhibitors SB202190 or SB203580, the protein kinase C inhibitors Calphostin C or H-7, or the phospholipase C inhibitor U-73122. PV IgG (25 µM) was then added and the cells were incubated for 30 mins at 37° C., and harvested in IEF lysis buffer. Extracts were separated on 10% SDS-PAGE gels followed by immunoblotting with anti-HSP27 and anti-phosphoHSP27 antibodies.

FIG. 4C presents results of native pore limit electrophoresis showing that PV IgG induced HSP27 phosphorylation alters HSP27 oligomerization. By native pore limit gel electrophoresis, both large and small oligomers of HSP27 were detected in the extracts (10 µg/lane) of cells incubated with buffer or control IgG. Decreased levels of large oligomeric HSP27 were observed in PV IgG cells.

FIG. 4D presents an autoradiogram of an immunoblot of an SDS-PAGE gel demonstrating that large oligomeric HSP27 can be readily visualized in buffer and control IgG treated keratinocytes, but not in PV IgG treated keratinocytes. Native extracts chemically cross-linked and subjected to reducing SDS-PAGE (5 µg protein/lane) and immunoblot analysis with HSP27 antibodies enhanced the detection of high molecular weight HSP27 oligomers whose levels were reduced in PV IgG treated cells.

Figure 5A:
Figure 5A:
Figure 5A:
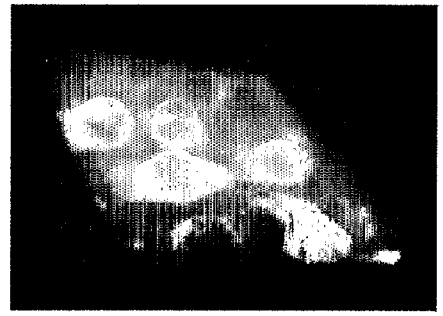
Figure 5A:
Figure 5A:
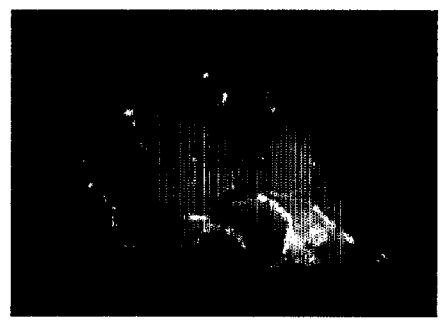
Figure 5A:
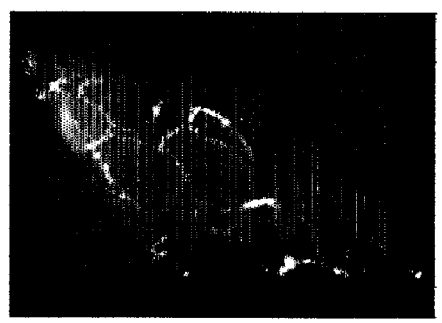
Figure 5B:
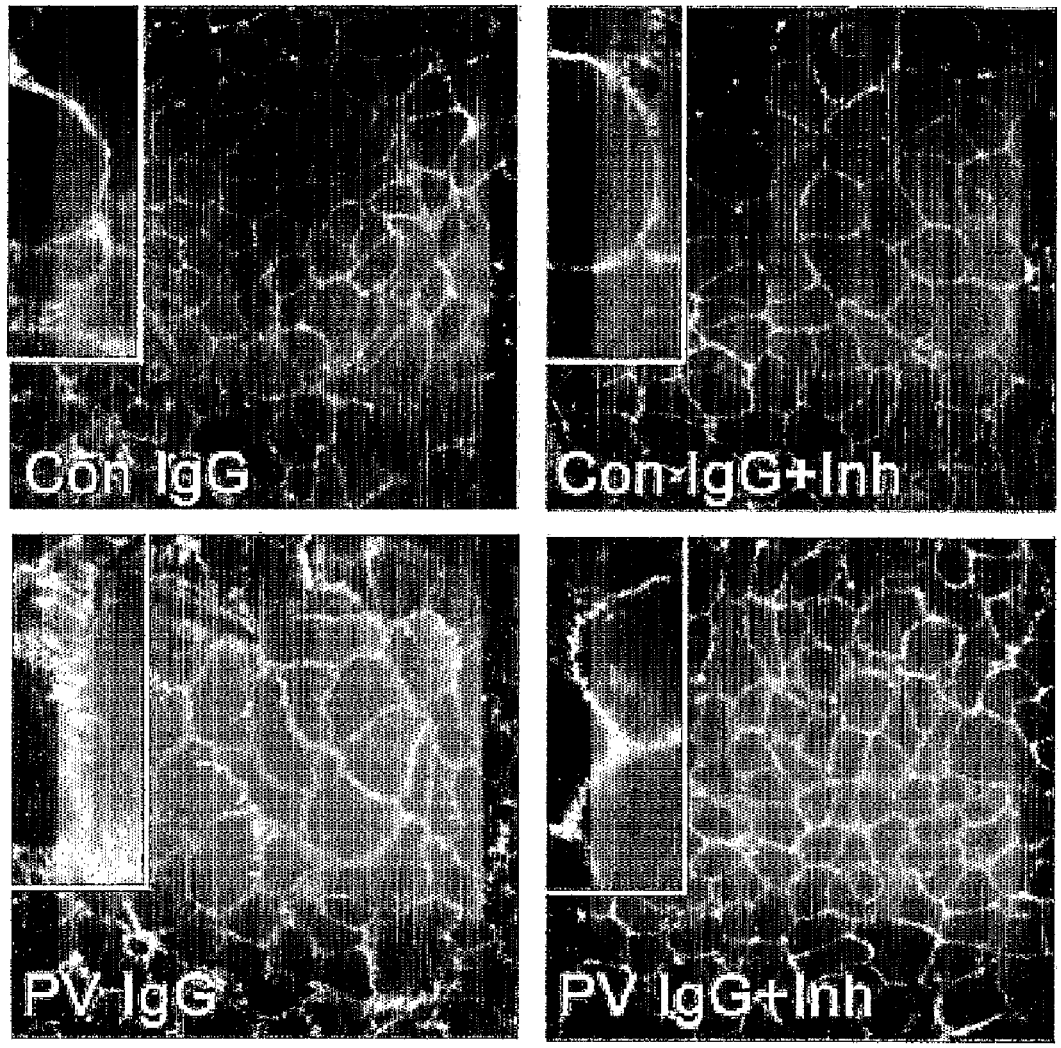
Figure 5C:
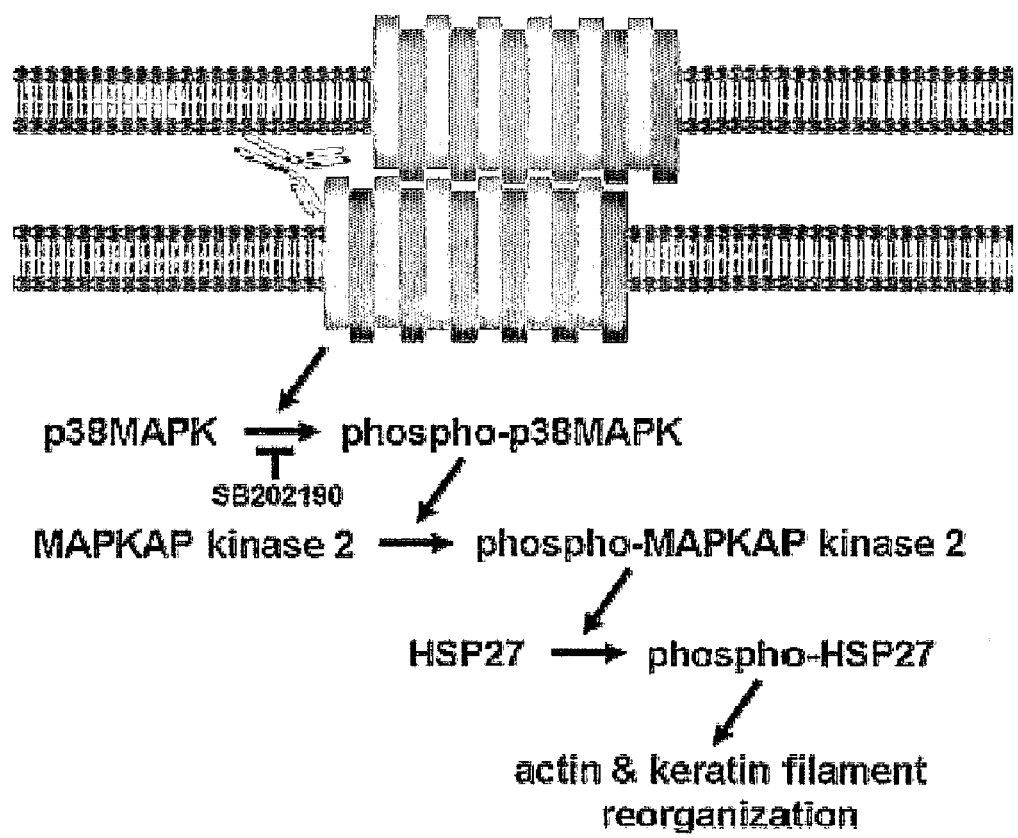

FIGS. 5A-5C are data showing that PV IgG induced cytoskeletal reorganization can be prevented by inhibiting p38MAPK. Keratinocytes were incubated with 25 µM control IgG (Con IgG) or 25 µM PV IgG (PV IgG) for 6 hrs at 37° C. or preincubated for 60 mins at 37° C. with the p38MAPK inhibitor SB202190 (100 µM) and then incubated with 25 µM control IgG (Con IgG+Inh) or 25 µM PV IgG (PV IgG+Inh) for 6 hrs. at 37° C. Cells were stained with the indicated antibodies or fluorescein-phalloidin and analyzed by confocal microscopy.

FIG. 5A is a photographic isometric view of the 3D reconstruction of serial confocal sections through keratinocytes treated with PV IgG or PV IgG+inhibitor (PV IgG+Inh) and shows that PV IgG induced keratin filament retraction is prevented by inhibiting p38MAPK. Cells were stained with antibodies to E-cadherin (E-cad) to delineate the cell membranes and keratin (Ker).

FIG. 5B is a series of photographs showing that phalloidin staining can be used to determine that PV IgG induced actin reorganization is prevented by inhibiting p38MAPK. The insets show magnification of actin staining at the cell-cell border. The membrane ruffling pattern of actin staining observed in the PV IgG treated cells is inhibited by blocking PV IgG signaling with SB202190.

FIG. 5C is a schematic diagram of proposed desmosome signaling. PV IgG binding to dsg3 within the desmosomes of two apposing cell membranes initiates a signaling cascade characterized by a sequential series of protein phosphorylation including phosphorylation of p38MAPK, which in turn phosphorylates MAPKAP kinase 2, which in turn directly phosphorylates HSP27. The biological effects of PV IgG induced HSP27 phosphorylation include dissociation of large oligomeric HSP27 to small oligomeric HSP27 and cytoskeletal reorganization associated with the cellular transition from cell-cell adhesion to acantholysis.

FIGS. 6A-6D show that inhibition of p38MAPK prevents blistering in pemphigus vulgaris passive transfer mice.

Figure 6A:
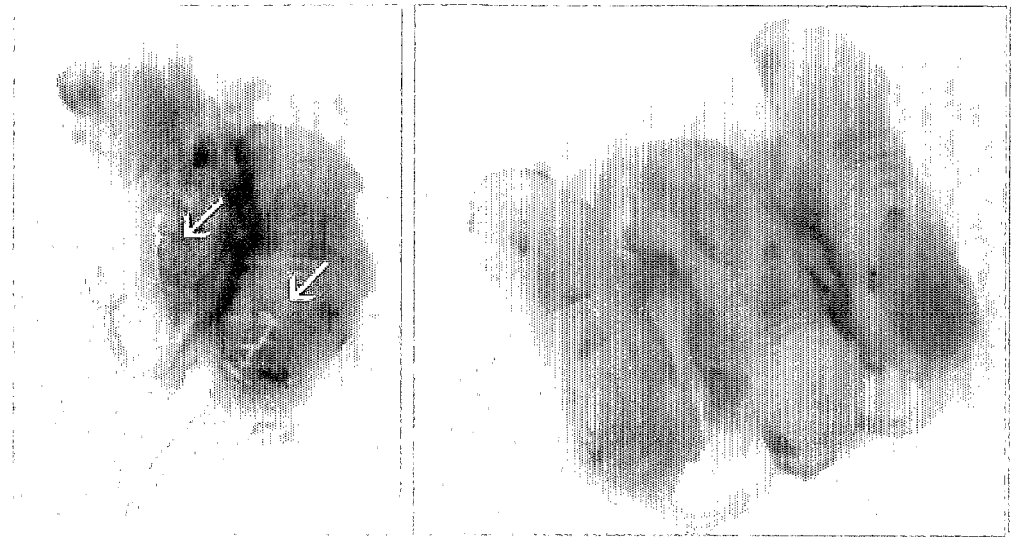

FIG. 6A is a series of photographs depicting neonatal C57BL/6J mice injected intradermally with either PV IgG (1.5 mg IgG/gram body weight) or PV IgG (1.5 mg IgG/gram body weight)+SB202190. When the mice were examined 18 hours later, the PV IgG treated mice show a positive Nikolsky's sign (white arrows) demonstrating loss of epithelial cell-cell adhesion. In contrast, mice treated with the SB202190 and PV IgG show a negative Nikolsky's sign indicating that the epithelial lesions remain intact.

Figure 6B:
Figure 6B:
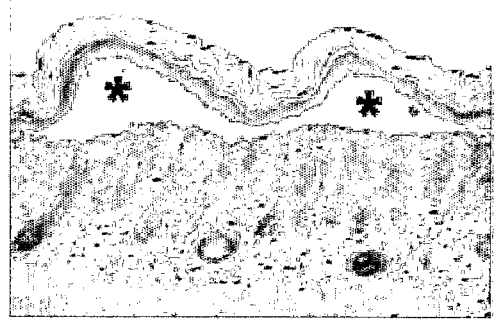
Figure 6B:
Figure 6B:
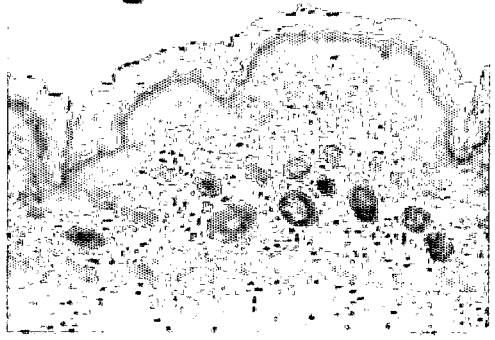

FIG. 6B is a series of photographs showing the skin biopsies of mice treated with control IgG (1 mg IgG/g body weight), PV IgG (1 mg IgG/g body weight), SB202190, or SB202190 and then PV IgG (1 mg IgG/g body weight) fixed in formalin and stained with hematoxylin and eosin. Suprabasal acantholysis leading to blister formation (*) can be seen in PV IgG treated mice, but is blocked in mice treated with SB202190 and PV IgG (PV IGG+SB202190).

Figure 6C:
Figure 6C:
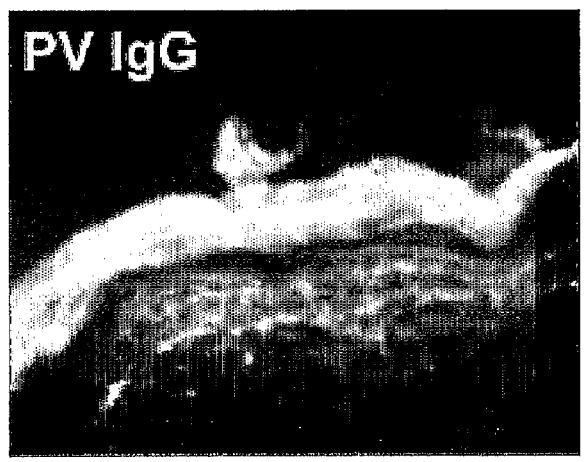
Figure 6C:

FIG. 6C is a series of photographs showing perilesional skin biopsies from control, PV IgG, and PV IgG+SB202190 treated mice examined for the presence of human anti-dsg3 PV IgG by direct immunofluorescence using a mouse anti-human Cy-2 conjugated monoclonal antibody. A honeycomb pattern of staining in the epidermis (arrows) is seen in both PV IgG and PV IgG+SB202190 treated mice, demonstrating that the inhibitor does not prevent binding of pemphigus vulgaris autoantibodies to the keratinocyte cell surface.

Figure 6D:
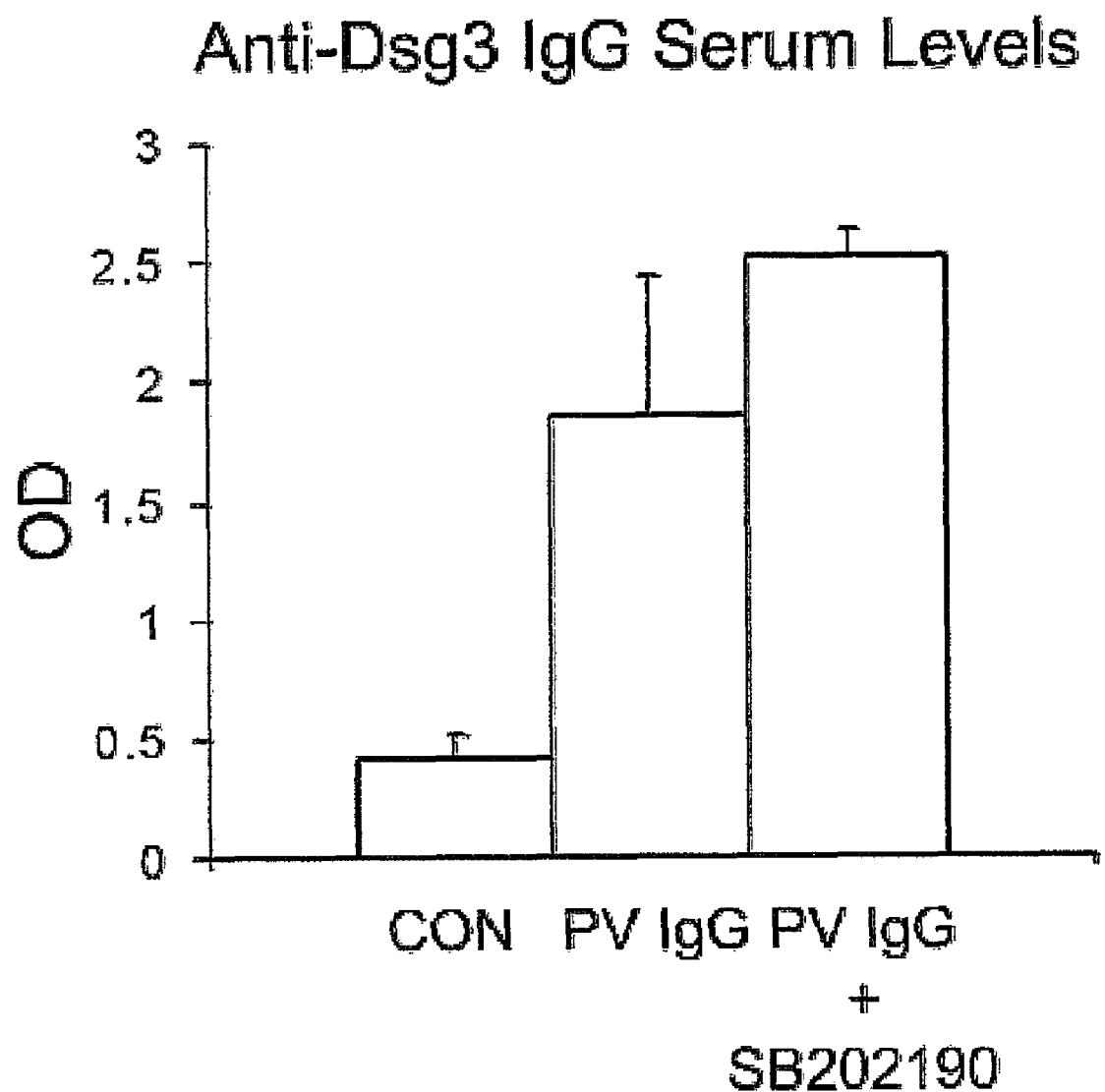

FIG. 6D is a bar graph depicting results from serum samples obtained from control, PV IgG and PV IgG+SB202190 treated mice examined for the presence of anti-dsg3 autoantibodies using a dsg3 ectodomain based ELISA assay (P value compared to control; n=3, S.D. shown by error bars.) (Arteaga, L. A. et al. (2002) $J$ $Invest$ $Dermatol$ 118, 806-811). P values calculated using student's T-test.

Figure 7A:
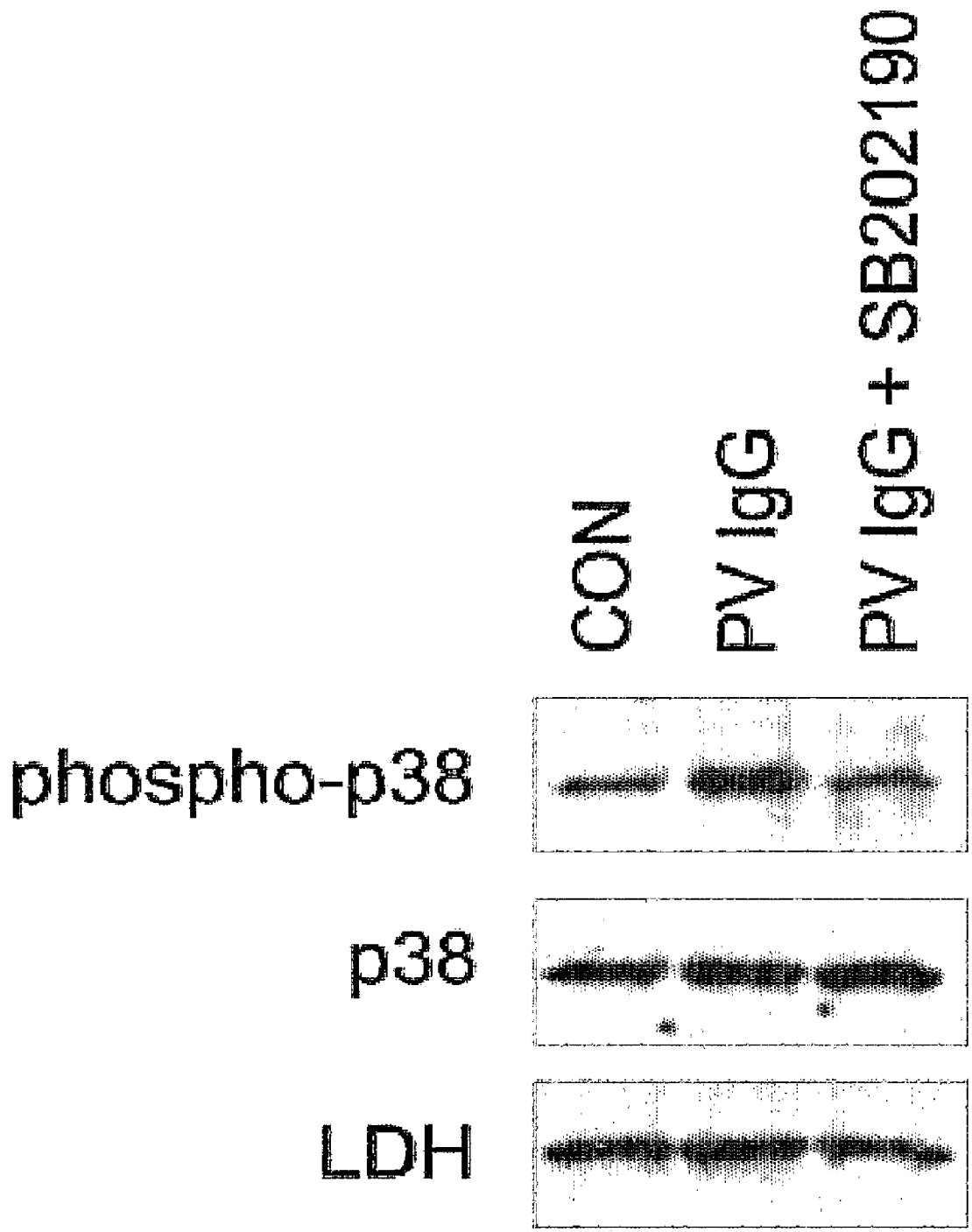
Figure 7B:
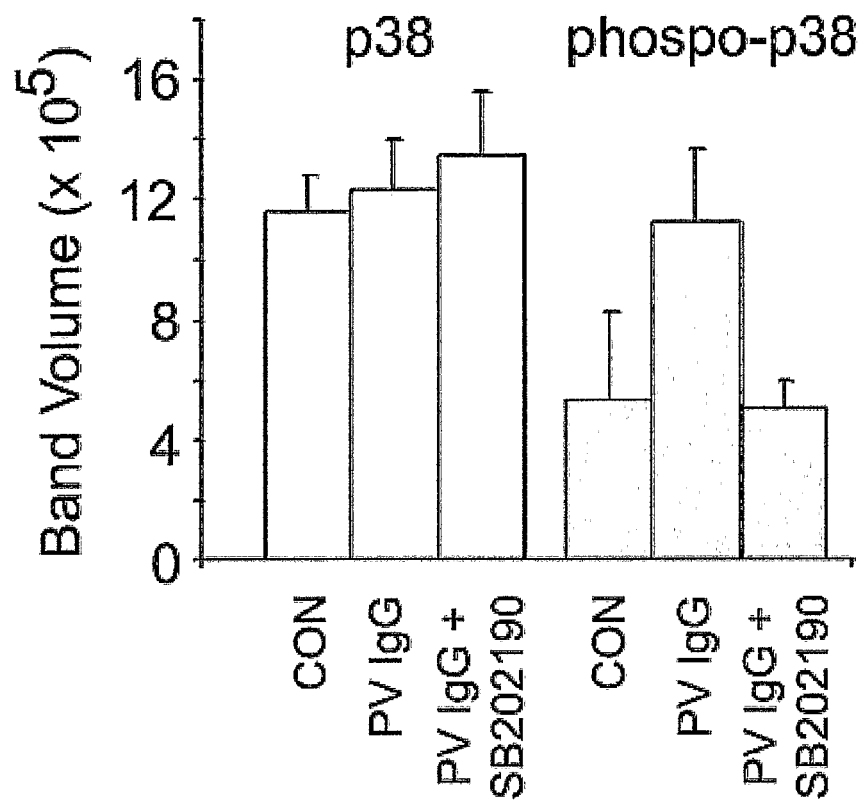
Figure 7C:
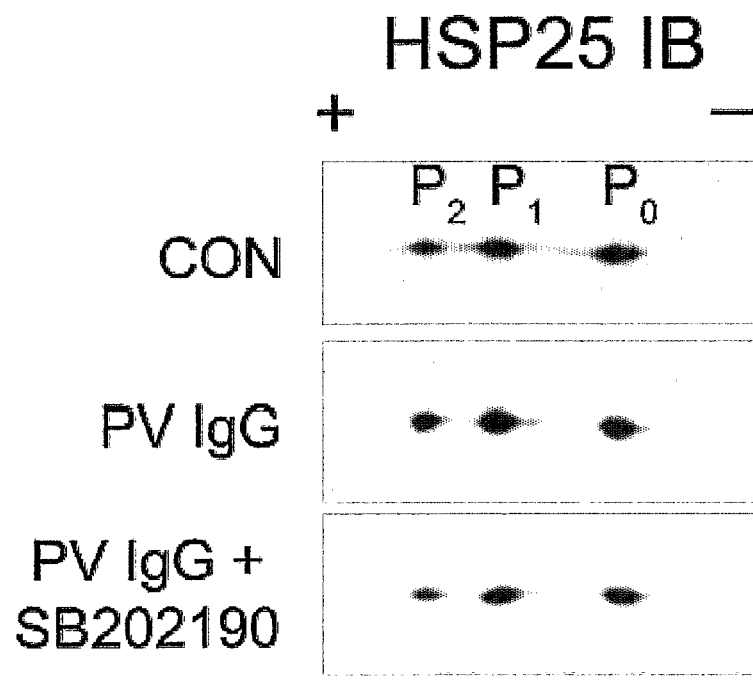

FIGS. 7A-7C disclose data demonstrating inhibition of PV IgG mediated p38MAPK and HSP27 phosphorylation in the skin of PV IgG+SB202190 treated neonatal C57/B6 wild type mice, wherein the mice were injected intradermally with either PV IgG (1.0 mg IgG/g body weight) or received an injection of SB202190 (6.25 µg in 50 µl PBS), followed 2 hours later by a second 50 µl intradermal injection of PV IgG (1.0 mg IgG/g body weight)+SB202190 (6.25 µg) in PBS. Skin biopsies were obtained after 18 hours of treatment and extracted in IEF lysis buffer.

FIG. 7A is an immunoblot showing LDH control, PV IgG, and PV IgG+SB202190 first equally loaded on and separated by SDS-PAGE, transferred to PVDF, and immunoblotted with antibodies to p38MAPK, phospho-p38MAPK or lactate dehydrogenase (LDH) as a loading control. Blots were developed by ECL reaction (Amersham, Piscataway, N.J., United States of America).

FIG. 7B is a bar graph illustrating signal intensity from the ECL reaction for each band from the immunoblot of FIG. 7A, quantified with a GeneGnome™ scanner (Syngene Bio Imaging, Frederick, Md., United States of America) using GeneSnap™ software (n=3, S.D. shown by error bars). The total levels of p38MAPK are similar in the control, PV IgG, and PV IgG+SB202190 treated mice. Increased amounts of phosphor-p38MAPK are present in PV IgG treated mice (P value compared to control). This increase is blocked in mice treated with SB202190 and PV IgG (no statistically significant difference for p38MAPK phosphorylation in PV IgG+SB202190 compared to controls, P=0.45, demonstrating in vivo block of p38MAPK phosphorylation).

FIG. 7C is an autoradiogram of an immunoblot showing cell extracts (30 µg) prepared and separated in the first dimension using 7 cm pH 4-7, non-linear IPGphor strips (Amersham Biosciences, Inc.) and in the second dimension by 10% SDS-PAGE followed by immunoblotting with antibodies to murine HSP25 using methods known in the art (see Berkowitz et al. (2005) $J$ $Biol$ $Chem$ 280, 23778-23784). Increased amounts of the most negatively charged HSP25 isoform ($P_2$) were observed in PV IgG treated mice and blocked in mice treated with PV IgG+SB202190. P values were calculated using student's T-test.

DETAILED DESCRIPTION

In the absence of a blistering disorder, the desmosome forms the site of adhesion between two cells in a subject and remains in an unactivated state. However, in subjects having blistering disorders, desmosome signaling is activated, resulting in acantholysis, which is the disruption of cell-cell adhesion, for example, in keratinocytes. As disclosed for the first time herein, the specific inhibition of the HSP27 phosphorylation pathway can prevent changes in the cytoskeleton associated with loss of cell-cell adhesion.

I. Definitions

It is to be understood that the terminology used herein is for the purpose of describing particular embodiments only and is not intended to be limiting.

Unless defined otherwise, all technical and scientific terms used herein have the same meaning as commonly understood to one of ordinary skill in the art to which the presently disclosed subject matter belongs.

Although any methods and materials similar or equivalent to those described herein can be used in the practice or testing of the presently disclosed subject matter, representative methods and materials are herein described.

Following long-standing patent law convention, the terms "a", "an", and "the" refer to "one or more" when used in this application, including the claims. Thus, for example, reference to "a carrier" includes mixtures of one or more carriers, two or more carriers, and the like.

Unless otherwise indicated, all numbers expressing quantities of ingredients, reaction conditions, and so forth used in the specification and claims are to be understood as being modified in all instances by the term "about". Accordingly, unless indicated to the contrary, the numerical parameters set forth in the present specification and attached claims are approximations that can vary depending upon the desired properties sought to be obtained by the presently disclosed subject matter.

The term "about", as used herein when referring to a measurable value such as an amount of weight, time, dose (e.g. radiation dose), etc. is meant to encompass in one example variations of ±20% or ±10%, in another example ±5%, in another example ±1%, and in yet another example ±0.1% from the specified amount, as such variations are appropriate to perform the disclosed method.

Further with respect to the therapeutic methods of the presently disclosed subject matter, a preferred subject is a vertebrate subject. A preferred vertebrate is warm-blooded; a preferred warm-blooded vertebrate is a mammal. The subject treated by the presently disclosed methods is desirably a human, although it is to be understood that the principles of the presently disclosed subject matter indicate effectiveness with respect to all vertebrate species which are to included in the term "subject." In this context, a vertebrate is understood to be any vertebrate species in which treatment of a blistering disorder is desirable. As used herein, the term "subject" includes both human and animal subjects. Thus, veterinary therapeutic uses are provided in accordance with the presently disclosed subject matter.

As such, the presently disclosed subject matter provides for the treatment of mammals such as humans, as well as those mammals of importance due to being endangered, such as Siberian tigers; of economical importance, such as animals raised on farms for consumption by humans; and/or animals of social importance to humans, such as animals kept as pets or in zoos. Examples of such animals include but are not limited to: carnivores such as cats and dogs; swine, including pigs, hogs, and wild boars; ruminants and/or ungulates such as cattle, oxen, sheep, giraffes, deer, goats, bison, and camels; and horses. Also provided is the treatment of birds, including the treatment of those kinds of birds that are endangered and/or kept in zoos, as well as fowl, and more particularly domesticated fowl, i.e., poultry, such as turkeys, chickens, ducks, geese, guinea fowl, and the like, as they are also of economical importance to humans. Thus, also provided is the treatment of livestock, including, but not limited to, domesticated swine, ruminants, ungulates, horses (including race horses), poultry, and the like.

As used herein, the term "blistering disorder" includes any disorder characterized by the presence of blisters and as would be apparent to one of ordinary skill in the art after a review of the present disclosure. Representative blistering disorders include, but are not limited to, autoimmune blistering disorders, such as pemphigus and pemphigoid autoimmune blistering disorders, as well as blistering resulting from exposure to biologic or chemical agents.

II. General Considerations

The presently disclosed subject matter relates generally to the discovery that desmosome mediated cell-cell adhesion is disrupted in blistering disorders, and that blocking phosphorylation of one or more components in the HSP27 phosphorylation pathway can effectively inhibit the desmosomal signal cascade associated with the development of a blistering disorder. By modulating the HSP27 phosphorylation pathway in a target tissue, it is possible to intervene in the blistering disorder, ameliorate the symptoms, and in some cases cure the disorder.

Where a blistering disorder such as pemphigus vulgaris is present in a subject, pathogenic anti-epidermal autoantibodies bind the dsg3 ectodomain of the desmosome. Changes in cellular adhesion structures then activate cellular signaling systems that link alterations in the state of cell adhesion to changes in cell behavior whereby cellular adhesion is altered. Where disruption of desmosome mediated cell-cell adhesion is the cause of, or contributes to, the development of blistering disorders, inhibition of disrupted cell-cell adhesion (referred to as "acantholysis") will reduce the deleterious effects of the disorder.

Examples of desmosome-associated disorders generally include blistering disorders, including autoimmune blistering disorders such as pemphigus vulgaris, pemphigus foliaceus, fogo selvagem, and paraneoplastic pemphigus wherein the body's own immune system produces antibodies that attack normal tissue as foreign. It is also provided that the disclosed methods can prove useful for blistering resulting from exposure to biologic or chemical agents.

As shown herein, it is possible to administer inhibitors of the HSP27 phosphorylation pathway that modulate of the desmosomal signal cascade associated with the development of blistering disorders. Prior to the discoveries of the presently disclosed subject matter, it was not known that development of a blistering disorder could be inhibited by blocking phosphorylation of one or more component in the HSP27 phosphorylation pathway to thereby inhibit the desmosomal signal cascade associated with the development of the blistering disorder.

As disclosed in the Examples, in a biochemical screen for changes in keratinocyte intracellular phosphorylation activated by binding of PV IgG to the desmosome adhesion protein dsg3, rapid time and PV IgG dose dependent phosphorylation of p38MAPK and HSP27 following binding of PV antibodies to cultured keratinocytes was identified. Inhibitors of p38MAPK were shown to prevent PV IgG induced phosphorylation of HSP27 and more importantly, prevent the early PV IgG induced cytoskeletal changes associated with loss of cell-cell adhesion. These observations suggest that inhibition of this signaling pathway in the tissue of a subject can be used to prevent end-organ damage (e.g. blistering) in blistering disorders such as PV.

The presently disclosed subject matter also provides for the practice of the disclosed methods in conjunction with other therapies, such as administration of conventional corticosteroids for control of a blistering disorder. Representative corticosteroids include prednisone, methylprednisolone, dexamethasone, and hydrocortisone. In some embodiments, the presently disclosed subject matter provides for the administration of reduced amounts of such corticosteroids as compared to conventional approaches.

III. Methods of Treatment

The presently disclosed subject matter provides for novel methods of treating a blistering disorder in a subject. More particularly, the methods of the presently disclosed subject matter involve the administration of a composition that inhibits activation of the HSP27 phosphorylation pathway to a target tissue in a subject to treat a blistering disorder. The composition is administered in an amount effective to inhibit the desmosomal signal cascade, which has been determined herein to be involved in the development of blistering disorders.

There are a variety of disorders in which activation of the desmosomal signal cascade associated with disrupted cell-cell adhesion is believed to be important, generally referred to herein as "blistering disorders". These disorders include, but are not limited to, autoimmune blistering disorders such as pemphigus and pemphigoid autoimmune blistering disorders wherein the hemidesmosome is targeted and wherein the body's own immune system produces antibodies that attack normal tissue as foreign. It is also provided that the disclosed methods can prove useful for blistering disorders resulting from exposure to biologic or chemical agents.

Thus, methods which inhibit phosphorylation of the HSP27 pathway can ameliorate symptoms and contribute to the cure of a blistering disorder. In one embodiment, the presently disclosed subject matter provides administering to a subject a composition that inhibits activation of the HSP27 phosphorylation pathway, whereby phosphorylation of HSP27 and the associated changes in HSP27 structure and cytoskeletal reorganization associated with blistering disorders are prevented.

Thus, in some embodiments, a target tissue to be treated is an epidermal or mucosal tissue in which blistering resulting from an underlying blistering disorder or from exposure to biologic or chemical agents is present. It is also understood that the tissue to be treated can be asymptomatic, lacking physical characteristics associated with the blistering disorder or the exposure to biologic or chemical agents.

Accordingly, a target tissue includes epidermal tissue, which includes the outer protective, nonvascular layer of the skin of vertebrates, covering the dermis. Also, a target tissue includes a mucosal tissue, which includes the tissue lining all vertebrate body passages that communicate with the exterior environment, such as the respiratory, genitourinary, and alimentary tracts, and having cells and associated glands that secrete mucus.

III.A. Compositions Inhibiting Activation of the HSP27 Phosphorylation Pathway

The presently disclosed methods can comprise administering therapeutic compositions which inhibit activation of the HSP27 phosphorylation pathway. Therapeutic compositions of the present invention are capable of containing a physiologically tolerable carrier, together with a composition capable of inhibiting activation of the HSP27 phosphorylation pathway as described herein.

The compositions of the presently disclosed subject matter can provide inhibition of the HSP27 phosphorylation pathway activation. Optionally, the inhibition of the pathway can occur by inhibiting phosphorylation of p38 MAPK. Suitable representative compositions include, but are not limited to, SB202190, SB203580, RWJ 67657, BIRB796, 681323, SCIO-469, SCIO-323, VX-702, VX-745, and KC706.

SB202190 (4-(4-Fluorophenyl)-2-(4-hydroxyphenyl)-5-(4-pyridyl)1H-imidazole) is a cell permeable pyridinyl imidazole of the formula $C_{20}H_{14}FN_3O$, which acts as a strong inhibitor of p38 MAPK. SB202190 is disclosed as a highly selective, potent and cell permeable inhibitor of p38 MAP kinase. Use and preparation of SB202190 is disclosed in U.S. Pat. No. 6,602,896, herein incorporated by reference.

SB203580 (4-(4-Fluorophenyl)-2-(4-methylsulfinylphenyl)-5-(4-pyridyl)1H-imidazole) is a selective p38 MAPK inhibitor of the formula $C_{22}H_{16}FN_3OS$. SB203580 is a widely used reference compound for p38 MAP kinase inhibition. The compound is available from Calbiochem (La Jolla, Calif., United States of America). SB203580 is referenced in Cuenda, A. et al. (1995) *FEBS Lett.* 364(2): 229-233; Young, P. R. et al. (1997) *J. Biol. Chem.* 272(18): 12116-12121; Ko, B. C., et al. (2002) *J. Biol. Chem.* 277(48): 46085-46092; Kogut, M. et al. (2002) *In. Immunopharmacol.* 2(7): 963-973; Knebel, A. et al. (2002) *Biochem. J.* 367(Pt.2): 525-532; Palladino, et al. (2003) *Nature Reviews Drug Discovery,* 2: 736-742.

RWJ 67657 is the compound also known as (4-[4-(4-fluorophenyl)-1-(2-phenylpropyl)-5-(4-pyridinyl)-1H-imidazol-2-yl]-3-butyn-1-ol), which acts as a highly selective and potent inhibitor of p38 MAP kinase. Use and preparation of RWJ 67657 is disclosed in PCT Application No. WO 98/47892, herein incorporated by reference. RWJ 67657 is commercially available through R.W. Johnson Pharmaceutical Research Institute (Raritan, N.J., United States of America).

BIRB796 is the compound also known as 1-(5-tert-butyl-2-p-tolyl-2H-pyrazol-3-yl)-3-[4-(2-morpholin-4-yl-ethoxy)-naphthalen-1-yl]-urea. Use and preparation of BIRB796 is disclosed in PCT Application No. WO 00/043384 and U.S. Pat. No. 6,319,921, herein incorporated by reference.

681323 is a p38 MAP kinase inhibitor, suitable for oral administration. The compound is currently involved in Phase II clinical trials. 681323 is available at GlaxoSmithKline (Research Triangle Park, N.C., United States of America). 681323 is referenced in Palladino, et al. (2003) *Nature Reviews Drug Discovery,* 2: 736-742.

SCIO-469 is a p38 MAP kinase inhibitor, suitable for oral administration. The compound is available through Scios, Inc. (Fremont, Calif., United States of America). SCIO-469 is referenced in Palladino, et al. (2003) *Nature Reviews Drug Discovery,* 2: 736-742.

SCIO-323 is a p38 MAP kinase inhibitor, suitable for oral administration. The compound is available through Scios, Inc. (Fremont, Calif., United States of America). SCIO-323 is referenced in Palladino, et al. (2003) *Nature Reviews Drug Discovery,* 2: 736-742.

VX-702 is a p38 MAP kinase inhibitor, suitable for oral administration. The compound is available through Vertex Pharmaceuticals, Inc. (Cambridge, Mass., United States of America). VX-702 is referenced in Palladino, et al. (2003) *Nature Reviews Drug Discovery,* 2: 736-742.

VX-745 is a p38 MAP kinase inhibitor, suitable for oral administration. The compound is available through Vertex Pharmaceuticals, Inc. (Cambridge, Mass., United States of America). VX-745 is referenced in Palladino, et al. (2003) *Nature Reviews Drug Discovery*, 2: 736-742.

KC706 is a p38 MAP kinase inhibitor, available through Kemia, Inc. (San Diego, Calif., United States of America). The compound is currently involved in Phase I clinical trials.

The compositions of the presently disclosed subject matter can provide inhibition of the HSP27 phosphorylation pathway activation.

Optionally, the inhibition of the HSP27 phosphorylation pathway can occur by inhibiting phosphorylation of MAP-KAP kinase 2. Representative compositions include, but are not limited to MAP Kinase-Activated Protein Kinase 2 C-Terminal (344-360) Blocking Peptide, 4-(2'-Fluorobiphenyl-4-yl)-N-(4-hydroxyphenyl)-butyramide.

MAP Kinase-Activated Protein Kinase 2 C-Terminal (344-360) Blocking Peptide is a synthetic peptide based on the human MAPKAPK-2 (amino acid residues 344-360) with a cysteine added. The peptide is represented by the formula $C_{91}H_{144}N_{24}O_{35}S_2$ and comprises the sequence (Cys)-Glu-Asp-Lys-Glu-Arg-Trp-Glu-Asp-Val-Lys-Glu-Glu-Met-Thr-Ser-Ala-Leu (SEQ ID NO:1). MAP Kinase-Activated Protein Kinase 2 C-Terminal (344-360) Blocking Peptide is available from Calbiochem (La Jolla, Calif., United States of America).

4-(2'-Fluorobiphenyl-4-yl)-N-(4-hydroxyphenyl)-butyramide is a p-amidophenolic compound that selectively inhibits the phosphorylation of MAPKAP Kinase 2 by p38 in a non-ATP-competitive manner. The compound is available from Calbiochem (La Jolla, Calif., United States of America). The compound is represented by the formula $C_{22}H_{20}FNO_2$.

Use and preparation of 4-(2'-Fluorobiphenyl-4-yl)-N-(4-hydroxyphenyl)-butyramide is disclosed in Davidson, W., et al. (2004) *Biochemistry* 43, 11658; and Lukas, S. M., et al. (2004) *Biochemistry* 43, 9950.

The compositions of the presently disclosed subject matter can provide inhibition of the HSP27 phosphorylation pathway activation. Optionally, the inhibition of the HSP27 phosphorylation pathway can occur by inhibiting phosphorylation of HSP27. Representative compositions include, but are not limited to HSP27 decoy phosphorylation substrates.

HSP27 decoy peptides act as competitive substrates for MAPKAP2, thereby preventing HSP27 from being phosphorylated. As disclosed, HSP27 decoy peptides are analogous to the HSP25 blocking peptide described in Hayess, K. and Benndorf, R. (1997) *Biochem. Pharmacol.* 53, 1239. One such HSP27 decoy peptide comprises the sequence Lys-Lys-Lys-Ala-Leu-Asn-Arg-Gln-Leu-Gly-Val-Ala-Ala (SEQ ID NO:2), and is available by Calbiochem (La Jolla, Calif., United States of America).

The therapeutic compositions of the presently disclosed subject matter can include pharmaceutically acceptable salts of the components therein. Pharmaceutically acceptable salts include the acid additions salts that are formed with inorganic acids such as, for example, hydrochloric or phosphoric acids, or such organic acids as acetic, tartaric, mandelic, and the like. Salts can also be derived from inorganic bases such as, for example, sodium, potassium, ammonium, calcium, or ferric hydroxides and such organic bases as isopropylamine, trimethylamine, 2-ethylamino ethanol, histidine, procaine and the like.

III.B. Administration

Representative dosages of the presently disclosed compounds are 1 to 10 µg/gram body weight for a mouse administered intradermally, using SB202190 as a particular example. It will be appreciated by one of skill in the art that dosage range will depend on the form of the inhibitor, and its potency. The dosage range is understood to be large enough to produce the desired effect in which the blistering disorder and the symptoms associated therewith are ameliorated, but not be so large as to cause adverse side effects. The appropriate range for therapeutic effectiveness will be readily determined by one skilled in the art depending on the route of administration, age, and condition of the subject being treated. The dosage can also be adjusted by the individual physician in the event of any complication. No unacceptable toxicological effects are expected when compositions disclosed herein are used in accordance with the presently disclosed subject matter.

The term "effective amount" is used herein to refers to an amount of the composition used in the disclosed methods sufficient to produce a measurable biological response. Actual dosage levels of active ingredients in a therapeutic composition of the presently disclosed subject matter can be varied so as to administer an amount of the active composition that is effective to achieve the desired therapeutic response for a particular subject and/or application. The selected dosage level will depend upon a variety of factors including the activity of the therapeutic composition, formulation, the route of administration, combination with other drugs or treatments, severity of the condition being treated, and the physical condition and prior medical history of the subject being treated. Preferably, a minimal dose is administered, and the dose is escalated in the absence of dose-limiting toxicity to a minimally effective amount. Determination and adjustment of a therapeutically effective dose, as well as evaluation of when and how to make such adjustments, are known to those of ordinary skill in the art.

For administration of a therapeutic composition as disclosed herein, conventional methods of extrapolating human dosage based on doses administered to a murine animal model can be carried out using the conversion factor for converting the mouse dosage to human dosage: Dose Human per kg=Dose Mouse per kg×12 (Freireich et al., (1966) *Cancer Chemother Rep.* 50:219-244). Drug doses can also be given in milligrams per square meter of body surface area because this method rather than body weight achieves a good correlation to certain metabolic and excretionary functions. Moreover, body surface area can be used as a common denominator for drug dosage in adults and children as well as in different animal species as described by Freireich et al. (Freireich et al., (1966) *Cancer Chemother Rep.* 50:219-244). Briefly, to express a mg/kg dose in any given species as the equivalent mg/sq m dose, multiply the dose by the appropriate km factor. In an adult human, 100 mg/kg is equivalent to 100 mg/kg×37 kg/sq m=3700 mg/m².

The compositions are administered in a manner compatible with the dosage formulation, and in a therapeutically effective amount. The quantity to be administered depends on the subject to be treated, capacity of the subject's system to utilize the active ingredient, and degree of therapeutic effect desired. Precise amounts of active ingredient required to be administered depend on the judgment of the practitioner and are peculiar to each subject. However, suitable dosage ranges for systemic application are disclosed herein and depend on the route of administration. Suitable regimes for administration are also variable, but are typified by an initial administration followed by repeated doses at 6 hour, 12 hour, or 24 hour intervals.

Insofar as an inhibitor of the HSP27 phosphorylation pathway can take the form of a mimetic or fragment thereof, it is to be appreciated that the potency, and therefore an expression of an "effective" amount can vary. However, as shown by the Examples, one skilled in the art can readily assess the potency of a candidate HSP27 phosphorylation inhibitor of the type presently envisioned by the presently disclosed subject matter.

Compositions used in the methods disclosed herein can be administered by any route suitable to the subject being treated and the nature of the disorder. Routes of administration include, but are not limited to, administration by injection, including intravenous, intraperitoneal, intramuscular, and subcutaneous injection, by transmucosal or transdermal delivery, topically, by nasal spray, suppository, and orally and the like.

Compositions used in the methods herein can comprise a composition that includes a pharmaceutically acceptable carrier. Suitable formulations include aqueous and non-aqueous sterile injection solutions that can contain antioxidants, buffers, bacteriostats, bactericidal antibiotics and solutes that render the formulation isotonic with the bodily fluids of the intended recipient; and aqueous and non-aqueous sterile suspensions, which can include suspending agents and thickening agents.

The compositions used in the methods can take such forms as suspensions, solutions or emulsions in oily or aqueous vehicles, and can contain formulatory agents such as suspending, stabilizing and/or dispersing agents. The compositions disclosed in the methods can also be formulated as a preparation for implantation or injection. Thus, for example, the compositions can be formulated with suitable polymeric or hydrophobic materials (e.g., as an emulsion in an acceptable oil) or ion exchange resins, or as sparingly soluble derivatives (e.g., as a sparingly soluble salt).

Alternatively, the active ingredient can be in powder form for constitution with a suitable vehicle, e.g., sterile pyrogen-free water, before use. Suitable formulations for each of these methods of administration may be found, for example, in *Remington: The Science and Practice of Pharmacy*, A. Gennaro, ed., 20th edition, Lippincott, Williams & Wilkins, Philadelphia, Pa.

IV. Methods of Modulation

The presently disclosed subject matter further relates generally to novel methods of modulating the HSP27 phosphorylation pathway. In some embodiments the methods comprise contacting a component selected from the group consisting of p38 MAPK, MAPKAP kinase 2, HSP27, or combinations thereof with a modulator, whereby the modulator specifically binds to the component to modulate the pathway.

As discussed in the Examples, modulators of p38MAPK are herein shown to prevent p38MAPK and HSP27 phosphorylation and further prevent PV IgG induced intermediate filament collapse and actin cytoskeletal remodeling within the target keratinocytes in vitro. Additionally, p38MAPK modulators as disclosed in the Examples prevent blistering disorders in vivo in neonatal mice passively transferred with pathogenic PV IgG.

As disclosed herein, the term "modulator" refers to a composition capable of binding, optionally specifically binding, to a component of the HSP27 phosphorylation pathway, selected from the group consisting of p38 MAPK, MAPKAP kinase 2, HSP27, or combinations thereof to thereby alter the HSP27 phosphorylation pathway. Thus, as used herein, the terms "modulate", "modulating" and "modulator" are meant to be construed to encompass inhibiting, blocking, or otherwise affecting signaling.

Such modulators can take a variety of forms that include compounds that interact with p38 MAPK, MAPKAP kinase 2, HSP27, or combinations thereof. Exemplary modulators suitable for the disclosed method are listed herein above.

EXAMPLES

The following Examples have been included to provide illustrations of the presently disclosed subject matter. In light of the present disclosure and the general level of skill in the art, those of skill will appreciate that the following Examples are intended to be exemplary only and that numerous changes, modifications and alterations can be employed without departing from the spirit and scope of the presently disclosed subject matter.

Materials And Methods For Examples 1-10

Materials

HSP27 antibodies were obtained from ABR (Golden, Colo., United States of America). Phospho-HSP27, p38MAPK, and phospho-p38MAPK antibodies were obtained from Cell Signaling Technology (Beverly, Mass., United States of America). SB202190, SB203580, Calphostin C, H-7, and U-73122 were obtained from Calbiochem (La Jolla, Calif., United States of America).

IgG Preparation

Pemphigus vulgaris sera (PV1, mucocutaneous PV; PV2, mucosal PV) were prepared as previously described (Ding et al., (1997) *Journal of Investigative Dermatology* 109, 592-596). PV IgG was purified from sera by ammonium sulfate precipitation followed by affinity chromatography on Protein G (HiTrap, Pharmacia, Piscataway, N.J., United States of America). IgG fractions were dialyzed against PBS, sterile filtered, and $CaCl_2$ added to a final concentration of 0.5 mM. Purity was confirmed by SDS-PAGE and activity assayed by indirect IF on sectioned monkey esophagus (PV1=1:640, PV2=1:5120). Control IgG (no activity by indirect IF) were prepared in parallel from normal human sera. Depleted PV IgG was prepared by removal of dsg3 ectodomain column (Ding et al., (1997) *Journal of Investigative Dermatology* 109, 592-596). The flow through was free of dsg3 specific IgG by negative indirect IF.

Tissue Culture

Normal primary human keratinocytes were passaged and expanded as described (Hu et al., (2001) *Journal of Investigative Dermatology* 117, 1059-1067). Third passage keratinocytes were grown to 80-90% confluence when dsg3, but not dsg1, was detected by Western blot of cell extracts using dsg3 and dsg1 specific monoclonal antibodies, respectively. $^{32}$[P]-$H_3PO_4$ was then added to the culture media (5 mCi/ml) and the cells incubated for 2 hours and either control IgG, PV IgG, or an equivalent volume of buffer added (to concentrations of 5, 10, or 25 μM). Cells were incubated for 15, 30, 60, or 150 minutes and then washed in PBS prior to harvesting in IEF lysis buffer (8M urea, 4% CHAPS, 2.5 mM DTT, 40 mM Tris, 10 μM E-64, 1 mM PMSF). Protein concentration was determined by modified Bradford assay as previously described (Hu et al., (2001) *Journal of Investigative Dermatology* 117, 1059-1067). IPG buffer (pH 3-10, non-linear; Pharmacia, Piscataway, N.J., United States of America) was added to each sample to a final concentration of 0.5% prior to isoelectric focusing. For inhibition studies, keratinocytes were pre-incubated for 60 mins at 37° C. with the p38MAPK inhibitors SB202190 (100 μM) or H-7 (10 μM), or the phospholipase C inhibitor U-73122 (4 μM), after which PV IgG was added to a final concentration of 25 μM, the cells incubated for 30 mins at 37° C., and harvested in IEF lysis buffer.

Two-Dimensional Gel Electrophoresis

40 μg of $^{32}$[P]-labeled extracts per gel were separated in the first dimension using 13 cm pH 3-10, non-linear IPGphor strips (Pharmacia, Piscataway, N.J., United States of America) and in the second dimension by 10% SDS-PAGE. Gels were dried and exposed to x-ray film and phosphoimage detection on a Molecular Dynamics Storm 840 phosphoimager. The ImageQuant (Molecular Dynamics, Sunnyvale, Calif., United States of America) program was used to quantify the radioactive signal detected from each spot on individual gels. The signal detected by the phosphoimager is expressed as spot volume and corresponds to the radioactive decay from the $^{32}$[P]-labeled protein in each spot. Statistical significance (p<0.05) was determined using the Student's T-test. Standards of known specific activity were spotted onto filter paper and used as internal controls for standardization amongst gel scans. Spots whose radioactivity remained constant amongst the various conditions served as internal controls.

Protein Identification 2D gel spots of interest were excised and digested with sequence grade trypsin and MALDI-TOF MS data acquired using a Q-tof Ultima Global instrument (Micromass/Waters Corp., Manchester, United Kingdom) as previously described (Karring et al., (2004) *Mol Cell Proteomics* 3, 660-674)

Native Gel Electrophoresis and Chemical Crosslinking

Keratinocytes grown to 80% confluence were incubated in the presence of 25 µM control IgG, 25 µM PV IgG, or an equivalent volume of buffer for 30 minutes, washed and harvested in PBS, and native extracts prepared by Dounce homogenization. Extracts (10 µg) from each sample were separated by native 4-20% gradient Tris-Glycine gel electrophoresis (Invitrogen, Inc., Carlsbad, Calif., United States of America), electrotransferred to PVDF, and subjected to Western blot analysis using anti-HSP27 antibodies. Native standards were from Pharmacia (HMW Native Electrophoresis Calibration Kit, Pharmacia, Piscataway, N.J., United States of America). Alternatively, HSP27 in native extracts was crosslinked as described (Lambert et al., (1999) *Journal of Biological Chemistry* 274, 9378-9385) by incubation in an equal volume of 0.1% gluteraldehyde in water for 30 mins at 30° C. The reaction was terminated with 1 volume of 1M Tris-HCl, 10% SDS, 10 mM EDTA for 5 mins at room temperature, separated by 4-20% gradient SDS-PAGE, electrotransferred to PVDF, and subjected to Western blot analysis using anti-HSP27 antibodies.

Confocal Microscopy

Keratinocytes grown to 100% confluence were incubated with 25 µM control IgG (Con IgG) or 25 µM PV IgG (PV IgG) for 6 hrs. at 37° C. or preincubated for 60 mins at 37° C. with the p38MAPK inhibitor SB202190 (100 µM) and then incubated with 25 µM control IgG (Con IgG+Inh) or 25 µM PV IgG (PV IgG+Inh) for 6 Ins. At 37° C. Cells were fixed and stained with flourescein conjugated phalloidin (Molecular Probes, Eugene, Oreg., United States of America), pancytokeratin antibodies (clone AE1/AE3, Zymed, San Francisco, Calif., United States of America), or goat anti-human E-cadherin antibodies (R & D Systems, mc, Minneapolis, Minn., United States of America) as previously described (Hu et al., (2001) *Experimental Nephrology* 9, 156-164), followed by Cy2 and Cy3 conjugated secondary antibodies (Jackson Laboratories, West Grove, Pa., United States of America). Images were analyzed using a Leica SP2 AOBS confocal microscope (Leica, Bannockburn, Ill., United States of America) with an excitation wavelength of 488 nm and capture at 500-550 nm or an excitation wavelength of 561 nm and capture at 590-650 nm using a 63×objective with NA 1.4. Double labeled samples were checked for bleed though by turning off the longer wavelength laser and assaying for the absence of image. For 3 dimensional image reconstructions, serial sections were scanned at 0.244 µm and rendered using the program Volocity Version 3 (Improvision, Lexington, Mass., United States of America).

Examples 1-8 dsg3 specific PV IgG were used to initiate structural changes in the desmosome. The keratinocyte extracts were then examined for changes in intracellular phosphorylation by culturing normal human keratinocytes in the presence of $^{32}$[P]-H$_3$PO$_4$ and exposing them to PV IgG. Phosphoimage analysis of 2D gel electrophoresis of $^{32}$[P]-labeled keratinocyte extracts was used to identify and quantify changes in protein phosphorylation.

FIGS. 1A-5 show that dsg3 specific pemphigus vulgaris IgG was successfully used to initiate structural changes in the desmosome. Keratinocyte extracts were examined for changes in intracellular phosphorylation by culturing normal human keratinocytes in the presence of $^{32}$[P]-H$_3$PO$_4$ and exposing the keratinocytes to pemphigus vulgaris IgG. Phosphoimage analysis of 2D gel electrophoresis of $^{32}$[P]-labeled keratinocyte extracts was used to identify and quantify changes in protein phosphorylation.

Example 1

PV IgG Alters Cellular Phosphorylation Patterns

At least three phosphorylation events occurred within 30 minutes of exposure of the keratinocytes to PV IgG (FIGS. 1A-1C) which precede loss of cell-cell adhesion as assessed by membrane retraction of apposing cells. Relative to buffer and normal IgG controls, PV IgG treated keratinocytes show increased phosphorylation in the proteins corresponding to Spots 2, 3, and 5 (FIGS. 1A-1C). No significant difference in phosphorylation was observed in spots 1 and 4 in control or PV IgG treated keratinocytes. Additionally, the phosphorylation of several spots (labeled with an asterisk "*" in FIG. 1A) did not change across time, dose, nor culture conditions and serve as internal controls.

Example 2

PV IgG-Induced Protein Phosphorylation is Dose Dependent

In order to examine the dose dependence of PV IgG induced protein phosphorylation, keratinocytes were incubated in the presence of 5, 10, or 25 µM PV or control IgG or buffer and examined for changes in phosphorylation by 2D electrophoresis (FIG. 1C). Dose dependent changes in protein phosphorylation of spots 2, 3, and 5 were observed in PV IgG treated cells, but not in cells treated with control IgG or in spots 1 and 4 in cells treated with either PV or control IgG. Accordingly, it was observed that PV IgG induced protein phosphorylation is dose dependent.

Example 3

PV IqG-Induced Protein Phosphorylation is Rapid and Transient

Figure 2A:
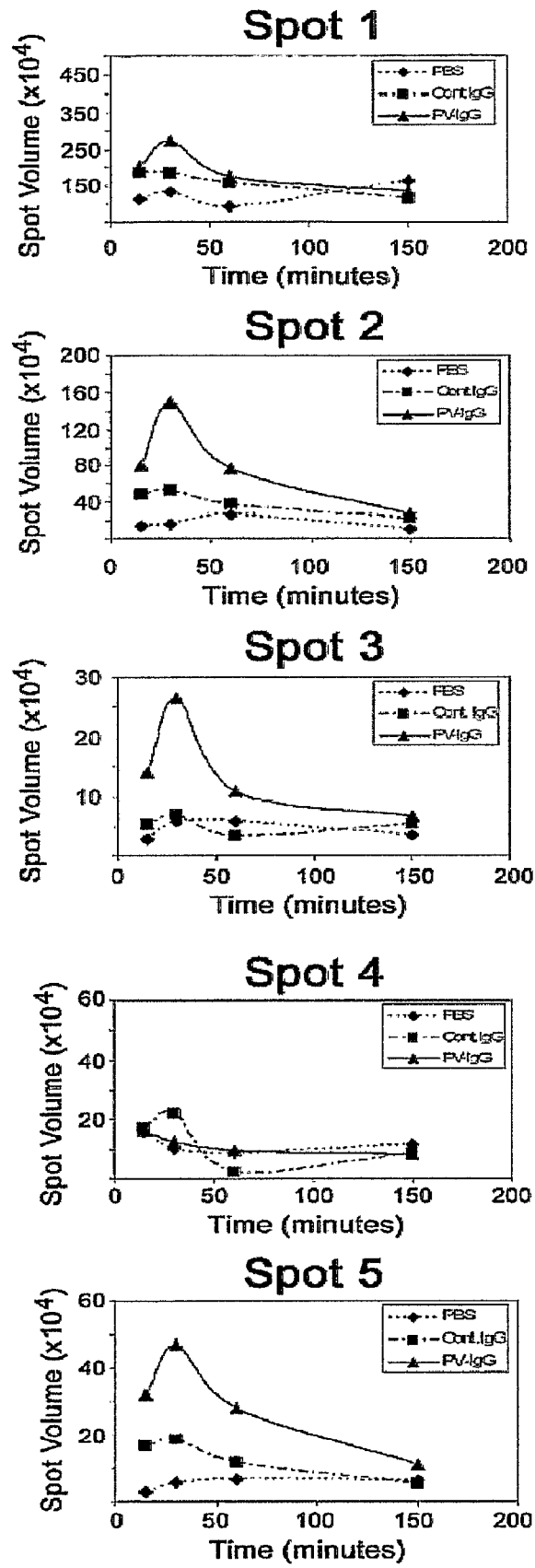
FIG. 2A is a series of graphs illustrating that pemphigus vulgaris IgG induced protein phosphorylation is rapid and transient. For the depicted time course, keratinocytes cultured in $^{32}[P]$-$H_3PO_4$ were treated with 25 μM G IgG, 25 μM control IgG, or buffer for 30, 60, and 150 minutes. Cell extracts were then separated on 2D gels and radioactivity was quantified by phosphoimage analysis. Pemphigus vulgaris IgG (PV IgG) is represented by the line corresponding to the triangles, control IgG (Cont IgG) is represented by the line corresponding to the squares, and buffer (PBS) is represented by the line corresponding to the diamonds.

In order to determine the time course of PV IgG-induced protein phosphorylation, keratinocytes were cultured in the presence of $^{32}$[P]-H$_3$PO$_4$ and 25 µM PV IgG, 25 µM control IgG, or buffer for 30, 60, and 150 minutes (FIG. 2A). Proteins corresponding to spots 2, 3, and 5 show a rapid rise in the phosphorylation that peaked within 30 minutes of addition to the media of PV IgG after which the levels of phosphorylation subsequently declined. No time dependent change was observed after addition of either control IgG or buffer. No notable change was observed in spots 1 and 4.

The increase and subsequent decrease in phosphorylation observed is consistent with a dynamic regulatory process and with the transient nature of protein post-translational modifications characteristic of intracellular signaling cascades. Other spots on the gel were not affected by the addition of PV IgG; i.e., no time or dose dependent phosphorylation changes were observed in the majority of the phosphoproteins resolved by 2D gel electrophoresis, indicating that the observed changes in phosphorylation did not result from a general increase in phosphorylation, but were specific for discrete cellular substrates. Accordingly, it was determined that PV IgG induced protein phosphorylation is rapid and transient.

Example 4

Protein Phosphorylation Requires anti-dsg3 Activity

Figure 2B:
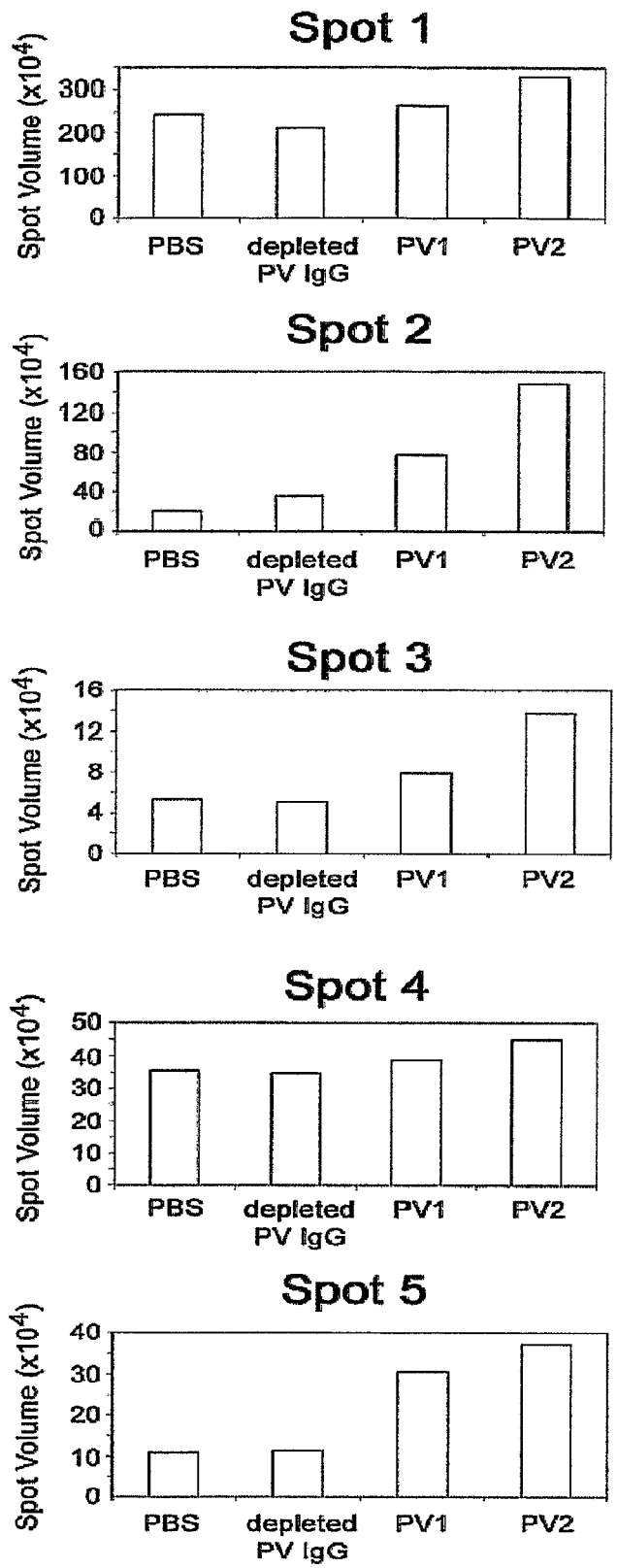
FIG. 2B is a series of graphs illustrating that protein phosphorylation requires anti-dsg3 activity. Keratinocytes, cultured in $^{32}[P]$-$H_3PO_4$, were exposed to buffer control, 25 μM pemphigus vulgaris IgG purified from the sera of two different patients (PV1 and PV2), or 25 μM pemphigus vulgaris IgG depleted of dsg3 specific antibodies by immunoabsorption for 30 mins. Depleted PV IgG was prepared by removal of dsg3 specific antibodies from sera PV2 by affinity chromatography on a recombinant dsg3 ectodomain column (as described in Ding, X., Aoki, V., Mascaro, J. M., Jr., Lopez-Swiderski, A., Diaz, L. A., and Fairley, J. A. (1997) *Journal of Investigative Dermatology* 109, 592-596). Cell extracts were then separated on 2D gels and the radioactive signal was quantified by phosphoimage analysis.

In order to determine whether PV IgG induced protein phosphorylation requires anti-dsg activity, the phosphorylation of spots 2, 3, and 5 was analyzed and found to be dependent upon PV IgG, as these phosphorylation events were not observed when samples were incubated with IgG or buffer controls nor when the PV IgG fractions were depleted of dsg3 specific antibodies by immunoabsorption (FIG. 2B). Additionally, PV IgG from two different PV patients stimulated the same pattern of phosphorylation and the level of phosphorylation correlated with their anti-dsg3 activity as determined by indirect IF. No notable difference was observed in spots 1 and 4, leading to the determination that protein phosphorylation requires anti-dsg activity.

Example 5

PV IgG Induces Phosphorylation of HSP27

Using gel tryptic digestion and MALDI-TOF, it was determined that the identity of spot 2 was HSP27. Western blot detection using antibodies to HSP27 and phospho-HSP27 confirmed the identity. After treatment of keratinocytes with PV IgG, increased signal was detected by 2D gel electrophoresis in the most acidic charge variant of HSP27 (FIG. 3A). Additionally, increased phospho-HSP27 reactivity was observed in PV IgG treated keratinocyte extracts when examined by Western blot of one dimensional SDS-PAGE (FIG. 3B).

Example 6

PV IgG Induced Phosphorylation of HSP27 Requires p38MAPK

Increased phosphor-p38MAPK was detected in PV IgG treated keratinocytes relative to controls (FIG. 4A) suggesting that PV IgG signaling to HSP27 is mediated by activated p38MAPK. It is noted that inhibition of p38MAPK inhibited the phosphorylation of HSP27 in keratinocytes exposed to PV IgG (FIG. 4B). No notable inhibition of HSP27 phosphorylation was observed in the presence of the protein kinase C inhibitors Calphostin C and H-7, nor the phospholipase C inhibitor U-73122.

Example 7

PV IqG Induced Phosphorylation of HSP27 is Associated with a Transition from Large to Small Oligomers The effects of PV IgG induced HSP27 phosphorylation on its oligomerization were investigated. On native pore limit gels, both large and small oligomers of HSP27 were detected in human keratinocytes incubated with buffer or control IgG. However, a decreased level of large oligomeric HSP27 was observed in PV IgG treated keratinocytes (FIG. 4C). The migration on the native gels is consistent with prior reports of large HSP27 oligomers of average Mr 530 kDa reduced to small oligomers of Mr 110 kDa by phosphorylation with MAPKAP kinase 2 (Rogalla et al., (1999) *J Biol Chem* 274, 18947-18956).

The large oligomeric isoform was not well detected by Western blot of native gels, perhaps due to the relative inefficiency of high molecular weight native proteins to undergo electrotransfer. Therefore, cross-linking was used to stabilize large oligomeric HSP27. Native extracts from keratinocytes were chemically cross-linked in gluteraldehyde and subjected to reducing SDS-PAGE and immunoblot analysis with HSP27 antibodies. This protocol enhanced the detection of high molecular weight HSP27 oligomers observed in buffer or control IgG treated cells, but markedly reduced detection of high molecular weight HSP27 oligomers in PV IgG treated keratinocytes (FIG. 4D).

Example 8

Inhibition of HSP27 Phosphorylation Blocks PV IgG Induced Keratin and Actin Reorganization In response to PV IgG, the keratin filament network of keratinocytes retracts from the cell membrane. This physiologic endpoint was used to determine whether the observed signaling events had a role in activating PV IgG-induced changes in the cytoskeleton. Consistent with previous reports (Caldelari et al. (2001) *Journal of Cell Biology* 153, 823-834), keratin filaments in PV IgG-treated keratinocytes were retracted from the membrane and demonstrated enhanced perinuclear localization. PV IgG-induced keratin filament retraction was prevented by the p38MAPK inhibitor SB202190 (FIG. 5A). Further, in PV IgG-treated keratinocytes phalloidin staining suggested that the actin cytoskeleton was undergoing reorganization consistent with the transition from stationary adherent cells to non-adherent migratory cells. PV IgG treatment was associated with a change from cortical staining to a pattern suggestive of ruffling membranes (Kozma et al., (1995) *Mol Cell Biol* 15, 1942-1952) (FIG. 5B). Notably, the PV IgG-inducted actin reorganization was similarly prevented by the p38 MAPK inhibitor SB202190 (FIG. 5*b*, PV IgG+Inh).

Discussion of Examples 1-8

Along with the demonstration that p38MAPK phosphorylates MAPKAP kinase 2, which in turn directly phosphorylates HSP27, the presently disclosed observations are consistent with a mechanism by which PV IgG binding to dsg3 activates "outside-in" desmosome signaling wherein (i) phosphorylation of p38MAPK leads to (ii) phosphorylation of MAPKAP kinase 2, which in turn (iii) phosphorylates HSP27 leading to (iv) changes in HSP27 quaternary structure and cytoskeletal rearrangements (FIG. 5C). Interestingly, endorepellin binding to $\alpha_2\beta_1$ integrin activates a signaling pathway in which p38MAPK and HSP27 phosphorylation are associated with structural changes in the actin cytoskeleton (Bix et al., 2004), suggesting that HSP27 could have a central role in cell adhesion junction signaling.

Because PV IgG specifically targets dsg3, the observed signaling events are proposed to result from changes in the desmosome. The precise nature of this structural change is unknown, but could include disruption of desmosomal protein-protein interactions or conformational changes within the target dsg3 molecule. The observation that specific inhibition of this pathway can prevent changes in the cytoskeleton associated with the transition form an adherent to non-adherent phenotype supports the hypothesis that the observed signaling events could be required for the loss of cell-cell adhesion induced in vivo by PV autoantibodies. This observation suggests that mechanisms in addition to steric hindrance could be required for PV IgG to mediate the loss of keratinocyte cell-cell adhesion and provides additional support that signaling plays a role.

Binding of specific pathogenic antibodies to dsg3 activates intracellular phosphorylation events suggesting that in addition to functioning in cell-cell adhesion, desmosomes are capable of acting as transmembrane receptors that transduce signals form the extracellular environment to the intracellular environment. Pharmacologic inhibition of PV IgG induced HSP27 phosphorylation can prove beneficial in the treatment of this severe and life threatening autoimmune disorder.

Example 9

P38 MAPK Inhibitors Block Blister Formation in vivo

The passive transfer PV mouse model developed by Anhalt and Diaz (Anhalt, et al. (1992) *New England Journal of Medicine* 306, 1189-1196) was used to test the hypothesis that p38MAPK inhibitors can block blister formation in vivo. In this model, the IgG fraction from patients and control non-affected normal individuals was purified and passively transferred into neonatal mice (Anhalt, et al. (1992) *New England Journal of Medicine* 306, 1189-1196; Rock, et al. (1990) *J of Clinical Investigation* 85, 296-299).

For in vivo inhibitor studies, the mice were injected intradermally with PV and normal IgG (1.0 or 1.5 mg/gram body weight) as disclosed in Mascaro et al. (*Clin Immunology & Immunopathology* 85, 90-96 (1997)). The P38 MAPK inhibitors were administered intradermally in two doses. In the first dose, 6.25 µg SB202190 was administered two hours prior to intradermal injection of IgG. In the second dose, 6.25 µg SB202190 was mixed with PV or control IgG and injected intradermally. Each animal received a total inhibitor dose of 12.5 µg.

After 18 hours, the skin of the neonatal mice from the test and control groups was examined clinically and histologically for the presence of cutaneous disease (FIG. 6). Perilesional skin biopsies were examined by direct immunofluorescence for the presence of PV IgG bound to the epidermal epithelium. Serum samples were collected from the test animals and analyzed for the presence of circulating anti-dsg3 antibodies by ELISA using the recombinant human dsg3 ectodomain using methods previously described by Arteaga et al. (*J Invest Dermatol* 118, 806-811 (2002)). Mice injected with PV IgG developed superficial blisters and a positive Nikolsky's sign (FIG. 6A, Table I). Histological examination revealed suprabasilar acantholysis (FIG. 6B, Table II). In contrast, mice treated with the p38MAPK inhibitor SB202190 and pathogenic PV IgG failed to develop blisters, clinically and histologically (FIGS. 6A,B and Table I, II).

Direct immunofluorescence of non-lesional skin from both PV IgG and PV IgG+SB202190 mouse skin demonstrated PV antibodies bound to epidermal keratinocyte cell membranes, indicating that the inhibitor did not prevent or alter the binding of autoantibodies to the target organ (FIG. 6C).

Furthermore, analysis of the serum samples showed a similar level of anti-dsg3 autoantibodies in the circulation of both PV IgG treated and PV IgG+SB202190 treated mice (FIG. 6D). The results indicate that the inhibitor did not prevent the diffusion of IgG to the target tissue, i.e. epidermis, nor did it inhibit the systemic absorption of the injected IgG, providing further support that the inhibitor was mediating its anti-acantholytic effects by targeting epidermal keratinocytes.

TABLE I

Numbers of Mice with Nikolsky Sign

|  | Nikolsky Positive | Nikolsky Negative |
|---|---|---|
| PV IgG | 11 | 1 |
| PV IgG + SB202190 | 1 | 11 |

TABLE II

Numbers of Mice with Suprabasilar Acantholysis

|  | Blisters Present | No Blisters |
|---|---|---|
| PV IgG | 11 | 1 |
| PV IgG + SB202190 | 1 | 11 |

Example 10

PV IgG Induced P38 MAPK and HSP27 Phosphorylation is Prevented in vivo by Pretreatment with SB202190

The phosphorylation state of p38MAPK and HSP25, the murine HSP27 homolog, was examined in order to determine whether PV IgG induced p38 MAPK and HSP27 phosphorylation is prevented in vivo by pretreatment with SB202190. Observations in human keratinocyte cell cultures have demonstrated that both p38 MAPK and HSP27 are phosphorylated when keratinocyte cultures are exposed to PV IgG. (See Examples 1-8 above).

Skin extracts from PV IgG treated mice demonstrated increased phosphorylation of both p38MAPK and HSP25 (FIGS. 7A, 7B, 7C). Equal amounts of total p38MAPK immunoreactivity was present in skin extracts from control, PV IgG and PV IgG+inhibitor treated mice. In contrast, increased phospho-p38MAPK immunoreactivity was observed in skin from PV IgG treated mice. This PV IgG-activated increase in p38MAPK phosphorylation was prevented by treating mice with the p38MAPK inhibitor SB202190 (FIGS. 7A, 7B), suggesting a role for p38 MAPK autophosphorylation (Ge et al. (2002) *Science* 295, 1291-1294) in the acantholytic process. When skin extracts were separated by two dimensional electrophoresis and immunoblotted with antibodies to HSP25, increased amounts of the most negatively charged HSP25 isoform where observed in PV IgG treated mice. Increased phosphorylation of the most negatively charged HSP25 isoform was inhibited in mice treated with PV IgG and the p38MAPK inhibitor SB202190.

Thus, both PV IgG induced p38 MAPK and HSP27 phosphorylation were prevented when mice were pretreated with SB202190 (FIG. 7).

Discussion of Examples 9 and 10

The molecular mechanisms by which dsg3 autoantibodies disrupt keratinocyte cell-cell adhesion has not been previously characterized. By incubating keratinocytes in the presence of $^{32}$[P]-H$_3$PO$_4$, changes in the phosphorylation pattern of cellular substrates after addition of purified PV IgG to keratinocyte cell cultures have been herein identified.

Several spots, resolved by 2D gel electrophoresis, were observed to undergo rapid changes in phosphorylation. The increase and subsequent decrease in phosphorylation observed is consistent with a dynamic regulatory process and with the transient nature of protein post-translational modifications characteristic of intracellular signaling cascades. Other spots on the gel were not affected by the addition of PV IgG; i.e., no time or dose dependent phosphorylation changes were observed in the majority of the phosphoproteins resolved by 2D gel electrophoresis, indicating that the observed changes in phosphorylation did not result from a general increase in phosphorylation, but were specific for discrete cellular substrates.

Specificity of the phosphorylation induced by anti-dsg3 pemphigus vulgaris antibodies was demonstrated by (i) the inability of either control IgG or PV IgG fractions depleted of dsg3 specific antibodies by immunoabsorption to stimulate phosphorylation of spots 2, 3, and 5; (ii) PV IgG purified from different pemphigus vulgaris patients stimulated the same pattern of phosphorylation; and (iii) the level of phosphorylation correlated with their anti-dsg3 activity. Because PV IgG specifically target dsg3, the observed phosphorylation/signaling events result from changes in the desmosome.

MALDI-TOF MS analysis of in gel tryptic digests was used to identify one of the disclosed phosphoproteins as HSP27. Identity was confirmed by immunoblotting with HSP27 and phospho-HSP27 specific monoclonal antibodies. The observation that HSP27 was rapidly and transiently phosphorylated in response to PV IgG suggests that p38MAPK can similarly be phosphorylated since phosphorylation of p38MAPK has previously been shown to phosphorylate MAPKAP kinase 2, which in turn phosphorylates HSP27. p38MAPK was similarly rapidly phosphorylated in keratinocytes exposed to PV IgG. Therefore, inhibitors of p38MAPK activity prevent PV IgG induced HSP27 phosphorylation.

HSP27 functions as a molecular chaperone to facilitate the refolding of denatured proteins, but also participates in signaling where it may regulate elements of the cytoskeleton including actin filaments (Benndorf et al. (1994) *J Biol Chem* 269, 20780-20784; Geum et al. (2002) *J Biol Chem* 277, 19913-19921; Panasenko et al. (2003) *Eur J Biochem* 270, 892-901) and keratin intermediate filaments (Perng, et al. (1999) *J Cell Sci* 112 (Pt 13), 2099-2112). Large oligomeric HSP27 has chaperone function, whereas small oligomeric HSP27 has direct signaling and cytoskeletal regulatory functions (Perng, et al. (1999) *J Cell Sci* 112 (Pt 13), 2099-2112; Duverger, et al. (2004) *J Biol Chem* 279, 10252-10260). Phosphorylation of HSP27 is considered to have a role in its ability to regulate the cytoskeleton (Lavoie, et al. (1993) *Journal of Biological Chemistry* 268, 24210-24214; Lavoie, et al. (1995) *Molecular & Cellular Biology* 15, 505-516; Guay et al. (1997) *Journal of Cell Science* 110, 357-368). Missense mutations in HSP27 lead to disrupted neurofilament assembly and cause the neuromuscular disorder Charcot-Marie Tooth disease as well as distal hereditary motor neuropathy providing additional support for the role of HSP27 in intermediate filament regulation (Evgrafov et al. (2004) *Nat Genet.* 36, 602-606).

As disclosed in the examples, inhibition of the desmosomal signaling cascade in vivo can be achieved by the methods described herein by administering HSP27 phosphorylation pathway inhibitors to a subject to prevent blister formation. For example, as disclosed herein, p38MAPK inhibitors prevent blistering disorders in vivo in neonatal mice passively transferred with pathogenic PV IgG. Therefore, inhibition of the keratinocyte desmosomal signaling pathway represents a new approach for treating blistering disorders.

REFERENCES

The references listed below as well as all references cited in the specification are incorporated herein by reference to the extent that they supplement, explain, provide a background for or teach methodology, techniques and/or compositions employed herein.

Anhalt, G. J., Labib, R. S., Voorhees, J. J., Beals, T. F. and Diaz, L. A. *New England Journal of Medicine* 306, 1189-1196 (1982).
Arteaga, L. A. et al. *J Invest Dermatol* 118, 806-811 (2002).
Benndorf, R., Hayess, K., Ryazantsev, S., Wieske, M., Behike, J., and Lutsch, G. (1994) *J Biol Chem* 269, 20780-20784.
Berkowitz, P. et al. (2005) *J Biol Chem* 280, 23778-23784.
Bix, G., Fu, J., Gonzalez, E. M., Macro, L., Barker, A., Campbell, S., Zutter, M. M., Santoro, S. A., Kim, J. K., Hook, M., Reed, C. C., and Iozzo, R. V. (2004) *J Cell Biol* 166, 97-109.
Caldelari, R., de Bruin, A., Baumann, D., Suter, M. M., Bierkamp, C., Balmer, V., and Muller, E. (2001) *Journal of Cell Biology* 153, 823-834.
Cuenda, A. et al. (1995) *FEBS Lett.* 364(2): 229-233.
Davidson, W. et al. (2004) *Biochemistry* 43, 11658.
Ding, X., Aoki, V., Mascaro, J. M., Jr., Lopez-Swiderski, A., Diaz, L. A., and Fairley, J. A. (1997) *Journal of Investigative Dermatology* 109, 592-596.
Duverger, O., Paslaru, L., and Morange, M. (2004) *J Biol Chem* 279, 10252-10260.
Evgrafov, O. V., Mersiyanova, I., Irobi, J., Van Den Bosch, L., Dierick, I., Leung, C. L., Schagina, O., Verpoorten, N., Van Impe, K., Fedotov, V., Dadali, E., Auer-Grumbach, M., Windpassinger, C., Wagner, K., Mitrovic, Z., Hilton-Jones, D., Talbot, K., Martin, J. J., Vasserman, N., Tverskaya, S., Polyakov, A., Liem, R. K., Gettemans, J., Robberecht, W., De Jonghe, P., and Timmerman, V. (2004) *Nat Genet.* 36, 602-606.
Eyre, R. W. & Stanley, J. R. (1988) *Journal of Clinical Investigation* 81, 807-812.
Freireich et al., (1966) *Cancer Chemother Rep.* 50, 219-244.
Ge, B. et al. *Science* 295, 1291-1294 (2002).
Gennaro, A. *Remington: The Science and Practice of Pharmacy*, ed., 20th edition, Lippincott, Williams & Wilkins, Philadelphia, Pa.
Geum, D., Son, G. H., and Kim, K. (2002) *J Biol Chem* 277, 19913-19921.
Guay, J., Lambert, H., Gingras-Breton, G., Lavoie, J. N., Huot, J., and Landry, J. (1997) *Journal of Cell Science* 110, 357-368.
Hayess, K. and Benndorf, R. (1997) *Biochem. Pharmacol.* 53, 1239.

Hu, E., Chen, Z., Fredrickson, T. A., Spurr, N., Gentle, S., Sims, M., Zhu, Y., Halsey, W., Van Horn, S., Mao, J., Sathe, G. M., and Brooks, D. P. (2001) *Experimental Nephrology* 9, 156-164.

Hu, P., O'Keefe, E. J., and Rubenstein, D. S. (2001) *Journal of Investigative Dermatology* 117, 1059-1067.

Karring, H., Thogersen, I. B., Klintworth, G. K., Enghild, J. J., and Moller-Pedersen, T. (2004) *Mol Cell Proteomics* 3, 660-674.

Knebel, A. et al. (2002) *Biochem. J.* 367(Pt. 2): 525-532.

Ko, B. C. et al. (2002) *J. Biol. Chem.* 277(48): 46085-46092.

Kogut, M. et al. (2002) *In. Immunopharmacol.* 2(7): 963-973.

Kozma, R., Ahmed, S., Best, A., and Lim, L. (1995) *Mol Cell Biol* 15, 1942-1952.

Lambert, H., Charette, S. J., Bernier, A. F., Guimond, A., and Landry, J. (1999) *Journal of Biological Chemistry* 274, 9378-9385.

Lavoie, J. N., Hickey, E., Weber, L. A., and Landry, J. (1993) *Journal of Biological Chemistry* 268, 24210-24214.

Lavoie, J. N., Lambert, H., Hickey, E., Weber, L. A., and Landry, J. (1995) *Molecular & Cellular Biology* 15, 505-516.

Lukas, S. M., et al. (2004) *Biochemistry* 43, 9950.

Mahoney, M. G., Wang, Z. H., and Stanley, J. R. *Journal of Investigative Dermatology* 113, 22-25 (1999).

Mascaro, J. M., Jr. et al. *Clinical Immunology & Immunopathology* 85, 90-96 (1997).

Palladino, et al. (2003) *Nature Reviews Drug Discovery* 2: 736-742.

Panasenko, O. O., Kim, M. V., Marston, S. B., and Gusev, N. B. (2003) *Eur J Biochem* 270, 892-901.

Perng, M. D., Cairns, L., van den, I. P., Prescott, A., Hutcheson, A. M., and Quinlan, R. A. (1999) *J Cell Sci* 112 (Pt 13), 2099-2112.

Rock, B., Labib, R. S., and Diaz, L. A. *Journal of Clinical Investigation* 85, 296-299 (1990).

Rogalla, T., Ehrnsperger, M., Preville, X., Kotlyarov, A., Lutsch, G., Ducasse, C., Paul, C., Wieske, M., Arrigo, A. P., Buchner, J., and Gaestel, M. (1999) *J Biol Chem* 274, 18947-18956.

Young, P. R. et al. (1997) *J. Biol. Chem.* 272(18): 12116-12121.

U.S. Pat. No. 6,602,896
U.S. Pat. No. 6,319,921
PCT Application No. WO 98/47892
PCT Application No. WO 00/043384

It will be understood that various details of the presently claimed subject matter can be changed without departing from the scope of the presently claimed subject matter. Furthermore, the foregoing description is for the purpose of illustration only, and not for the purpose of limitation.

---

---

What is claimed is:

1. A method of treating a blistering disorder, comprising:
   a) providing a subject suffering from a blistering disorder, wherein the blistering disorder is an autoimmune blistering disorder; and
   b) administering to a target tissue in the subject an effective amount of a composition that inhibits activation of a HSP27 phosphorylation pathway in the target tissue.

2. The method of claim 1, wherein the inhibitor of the HSP27 phosphorylation pathway inhibits a desmosomal signal cascade.

3. The method of claim 1, wherein the autoimmune blistering disorder is selected from the group consisting of pemphigus and pemphigoid autoimmune blistering disorders.

4. The method of claim 1, wherein the subject is a mammal.

5. The method of claim 1, wherein the composition which inhibits the HSP27 phosphorylation pathway inhibits phosphorylation of p38 MAPK.

6. The method of claim 5, wherein the p38 MAPK phosphorylation inhibitor is selected from the group consisting of SB202190, SB203580, RWJ 67657, BIRB796, 681323, SCIO-469, SCIO-323, VX-702, VX-745, and KC706.

7. The method of claim 1, wherein the composition which inhibits activation of the HSP27 phosphorylation pathway inhibits phosphorylation of HSP27.

8. The method of claim 1, wherein the composition which inhibits activation of the HSP27 phosphorylation pathway inhibits phosphorylation of MAPKAP Kinase 2.

9. The method of claim 1, wherein the composition which inhibits activation of the HSP27 phosphorylation pathway is administered by subcutaneous injection, intravenous injection, intraperitoneal injection, intramuscular injection, topical application, transmucosal application, transdermal application, suppository, nasal spray, orally, or combinations thereof.

10. The method of claim 9, wherein the composition which inhibits activation of the HSP27 phosphorylation pathway comprises a pharmaceutically acceptable carrier.

11. The method of claim 1, wherein the administering is conducted in conjunction with corticosteroids.

12. The method of claim 11, wherein the corticosteroids are selected from the group consisting of prednisone, methylprednisolone, dexamethasone, and hydrocortisone.

13. The method of claim 1, wherein the target tissue is skin or mucosa.

* * * * *